US 6,673,595 B2

(12) United States Patent
Barbera-Guillem

(10) Patent No.: US 6,673,595 B2
(45) Date of Patent: Jan. 6, 2004

(54) AUTOMATED CELL MANAGEMENT SYSTEM FOR GROWTH AND MANIPULATION OF CULTURED CELLS

(75) Inventor: Emilio Barbera-Guillem, Powell, OH (US)

(73) Assignee: Biocrystal, LTD, Westerville, OH (US)

(*) Notice: Subject to any disclaimer, the term of this patent is extended or adjusted under 35 U.S.C. 154(b) by 274 days.

(21) Appl. No.: 09/940,388

(22) Filed: Aug. 27, 2001

(65) Prior Publication Data

US 2003/0040104 A1 Feb. 27, 2003

(51) Int. Cl.[7] .................................................. C12M 1/36
(52) U.S. Cl. ............................ 435/286.2; 435/287.3; 435/303.1
(58) Field of Search .................... 435/284.1, 286.1, 435/286.2, 287.3, 303.1

(56) References Cited

U.S. PATENT DOCUMENTS

| | | | |
|---|---|---|---|
| 4,090,921 A | 5/1978 | Sawamura et al. | |
| 4,676,951 A | * 6/1987 | Armes et al. | ................. 422/65 |
| 4,696,902 A | 9/1987 | Bisconte | ..................... 435/300 |
| 4,800,164 A | 1/1989 | Bisconte | ..................... 435/300 |
| 4,812,392 A | 3/1989 | Miyake et al. | ................. 435/3 |
| 4,966,853 A | 10/1990 | Matsuda et al. | ............. 435/284 |
| 5,424,209 A | 6/1995 | Kearney | ..................... 435/284 |
| 5,573,950 A | * 11/1996 | Graessle et al. | ......... 435/287.3 |
| 6,008,010 A | 12/1999 | Greenberger et al. | ......... 435/41 |

FOREIGN PATENT DOCUMENTS

WO    WO/00/56870    9/2000

* cited by examiner

Primary Examiner—David A. Redding
(74) Attorney, Agent, or Firm—Benesch, Friedlander, Coplan & Aronoff, LLP

(57) ABSTRACT

An automated cell management system which can be programmed to perform and control various operations of the essential phases of cell culturing, of cell culture manipulation, and of cell culture evaluation. The automated cell management system comprises a housing, a storage array for accommodating a plurality of cell culture devices, a loading station, a means for harvesting one or more components from a cell culture device, and one or more processing stations. The automated cell management system may further comprise mechanism for tracking each cell culture device, a plurality of reservoirs, a centrifuge, a microprocessor, one or more evaluation stations, one or more means for sterilization, and a combination thereof.

68 Claims, 8 Drawing Sheets

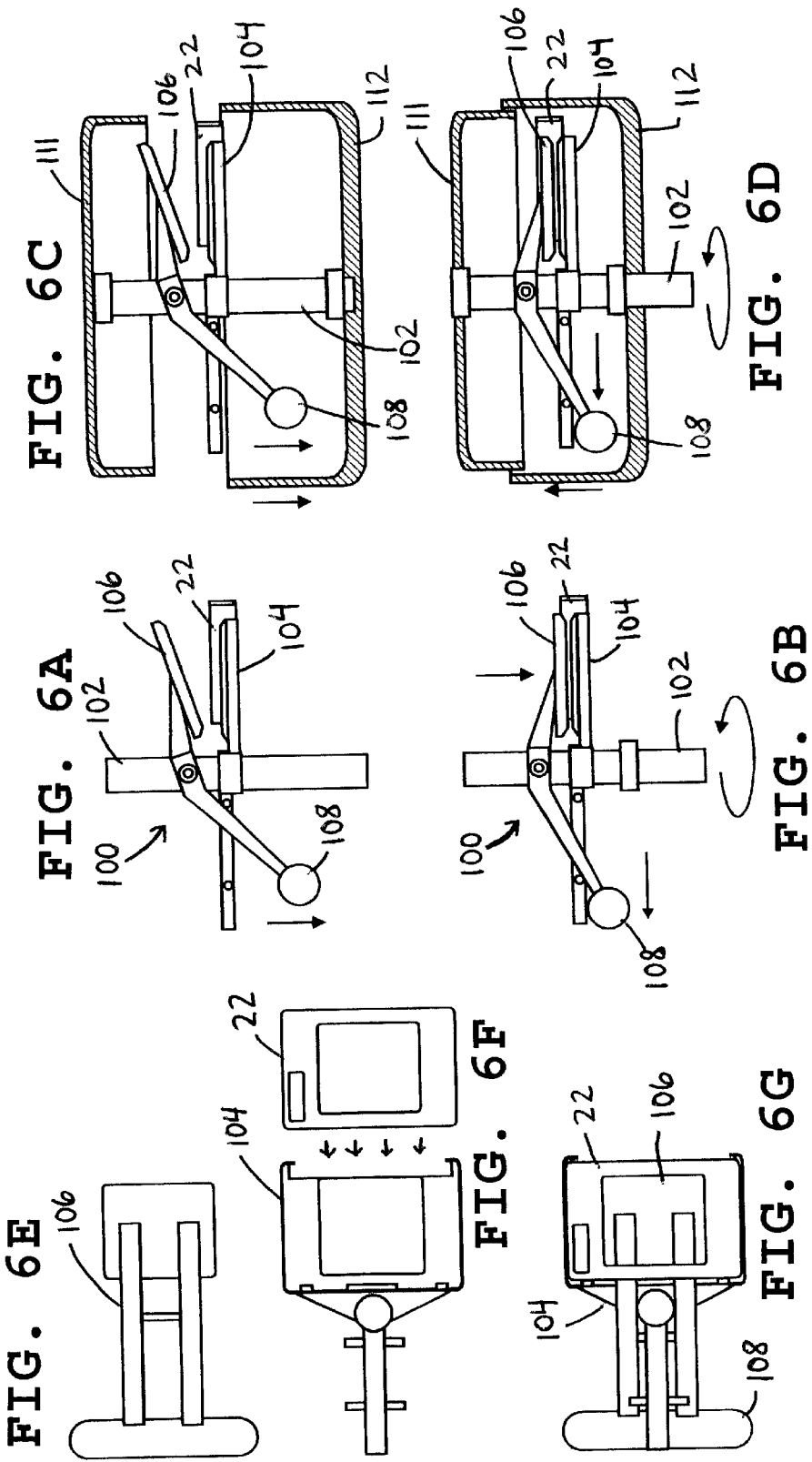

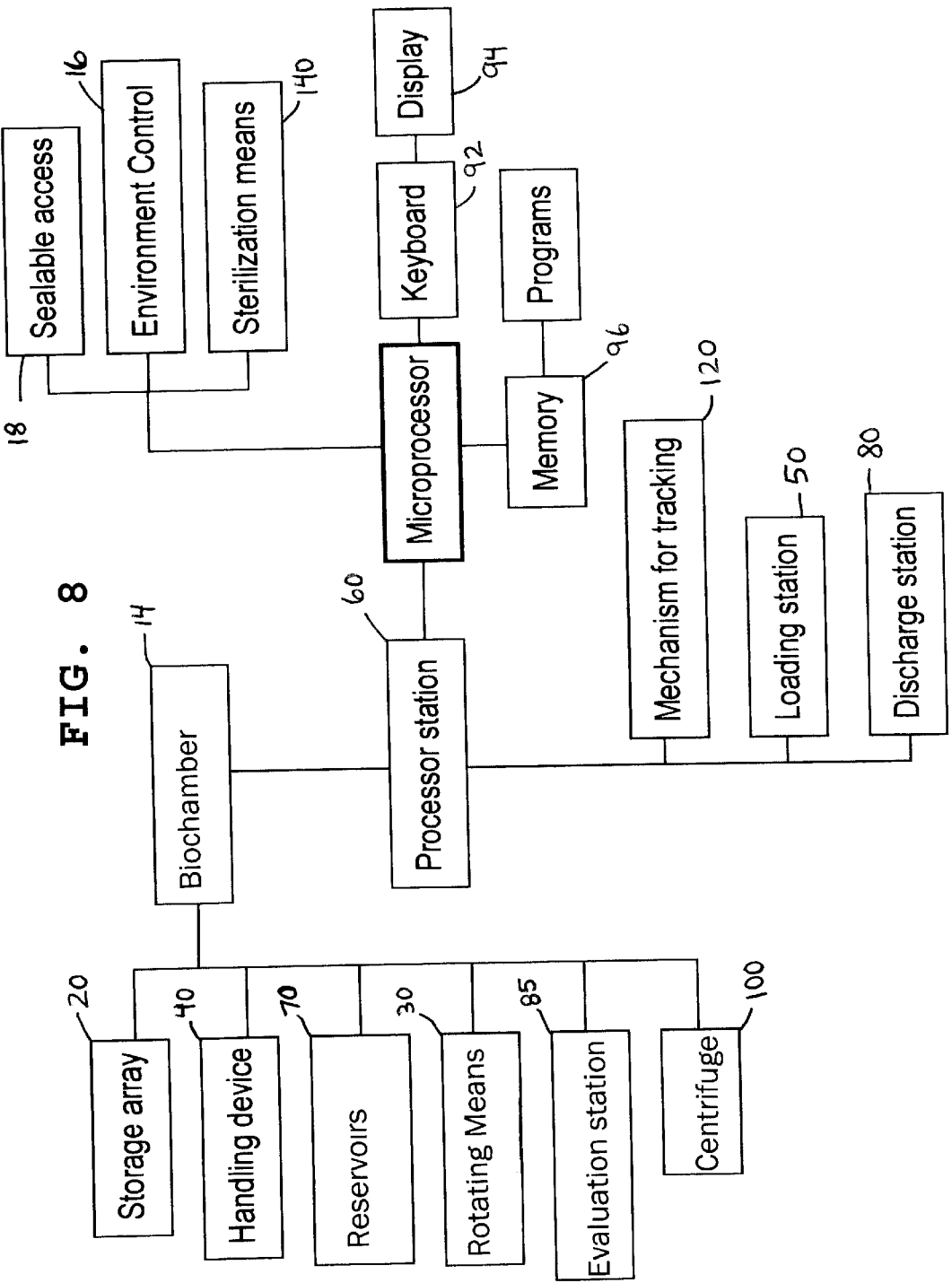

AUTOMATED CELL MANAGEMENT SYSTEM FOR GROWTH AND MANIPULATION OF CULTURED CELLS

FIELD OF THE INVENTION

The present invention generally relates to the field of cell culture; and more particularly to an automated system for management of culturing cells and manipulating the cultured cells.

BACKGROUND OF THE INVENTION

Basic operations for culturing cells may include, but are not limited to, initiation of a cell culture, maintenance of cell culture (e.g., storage under appropriate environmental conditions, replacement with tissue culture medium to renew nutrient availability, when desired in promoting cell growth), harvesting (e.g., harvesting the cultured cells and/or cell culture medium, particularly when the culture medium contains a substance produced by the cultured cells), and termination of the cell culture. A cell culture may be manipulated by one or more means that may include, but is not limited to: changing the environmental conditions to which the cell culture is exposed; treating the cultured cells with a biological substance for either evaluating the effect of the substance on the cultured cells, or for inducing the cultured cells to respond in a morphological, physiological, biological, or biochemical manner; and evaluating cultured cells by detecting and/or measuring ("determining") one or more cell culture parameters which comprises one or more parameters of cultured cells and/or one or more parameters of the cell culture medium. As known to those skilled in the art, a parameter of cultured cells may include, but is not limited to, growth rate, morphology (e.g., size, shape, and the like), state of differentiation, granularity, migration, light scatter, attachment (anchorage-dependency or lack thereof), and the like. A parameter of the cell culture medium may comprise a chemical, biological, or physical characteristic of the medium (including, but not limited to, pH, oxygen content, $CO_2$ content, nutrient content (e.g., glucose), and the like); or the presence of a product of cultured cells which is secreted, excreted, or released into the cell culture medium (including, but not limited to, metabolite, cytokine, recombinant product (e.g., protein, peptide, and the like), and the like). In culturing and manipulating cells, performed is a sequence of dissociated operations, wherein the sequence may be varied depending on the desired objective.

Genomics, proteomics, and drug discovery are generating a need for expanded versatility of applications for manipulating cell cultures, as well as a greater need for efficient and economical growth of cultured cells in high volume ("high-throughput cell culture"). For example, in developing and testing one or more biological substances (e.g., including, but not limited to, genetic vectors, genetic sequences, vaccines, drugs, growth factors, cytokines, chemicals, enzymes, or the like), it may often be desirable to evaluate the response of cultured cells after treatment with a biological substance; and additionally to evaluate the responses in a multitude of treated cell cultures being grown simultaneously. It is known in the art (see, e.g., *Genetic Engineering News* 20:26, Sep. 1, 2000) that while a large cell culture lab may be able to handle simultaneously a few dozen cell cultures, the present systems are not adequate to meet industry's current demands for high-throughput cell culture. Despite advances in bioautomation technology, a bottleneck in implementing high-throughput cell culture is a lack of automated systems which maximize the number of cell cultures that can be grown and manipulated simultaneously. Thus, not only is there a need for an automated system for carrying out basic operations for culturing cells, there is also a need for an automated system for manipulating cultured cells (e.g., treating cultured cells with one or more biological substances, and may further include evaluating cultured cells for one or more cell culture parameters). Such an automated system would be capable of, as an integrated unit, performing dissociated operations associated with culturing cells and with manipulating cultured cells.

Conventional cell culture devices and manual methods for culture are not adequate for high-throughput cell culture. In a manual method of culturing cells, a cell culture device containing cultured cells is removed from a controlled environment (e.g., that maintains a specific atmosphere, temperature, and humidity) provided by a conventional tissue culture incubator. Thus, once removed from this controlled environment, the cultured cells may be subject to a rapid change in the environment. Currently, to perform one or more operations of cell culturing (e.g., removal of cell culture medium, addition of fresh tissue culture medium, removal of cultured cells, addition of cells to be cultured, and the like), it is first necessary to open the cell culture device to allow for pipetting. In that regard, conventional cell culture devices, such as flasks and roller bottles, have screw caps which require temporary removal to allow for pipetting of one or more of tissue culture medium, cell culture medium, or cells into or out of the cell culture device. Thus, opening and closing a number of cell culture devices during routine culturing is highly labor intensive, and necessitates an open system, at least part of the time, which greatly increases a breach in the maintenance of sterility of the cultures. Further, in a harvesting operation which requires separation of substantially all of the cell culture medium from the cultured cells (e.g., in harvesting the cell culture medium and/or the cells), transfer of the cell culture to and from a vessel for centrifugation is required. This "harvesting" operation represents additional time in which the cells are removed from a controlled environment, and represents an additional risk in breaching the maintenance of sterility of the culture. Additionally, due to the relative inefficient gas transfer through the screw cap, a large volume of air space (relative to the growth surface) is required in conventional cell culture devices; and hence, their overall size is rather bulky. Therefore, a tissue culture incubator can accommodate only a relatively limited number of conventional cell culture devices simultaneously, in adding to the difficulty and expense of high-throughput cell culture.

Thus, there is a need for an automated system for performing basic operations for culturing cells, and which may be used for high-throughput cell culture.

SUMMARY OF THE INVENTION

The present invention provides an automated system for management of cell cultures ("an automated cell management system"). The terms "cell management" and "management of cell cultures" are used synonymously to mean that the automated system of the present invention can perform operations for culturing cells, and operations for manipulating cell cultures, as will be more apparent from the following descriptions. Thus, provided is an automated system for culturing cells, and manipulating cell cultures.

It is a primary object of the invention to provide an automated system that may be used for high-throughput cell culture.

It is another object of the present invention to provide an automated cell management system capable of integrating into one unit the capability to perform dissociated operations of cell culturing and cell culture manipulation.

It is another object of the present invention to provide an automated cell management system that can be programmed to perform and control various operations of cell culturing and cell culture manipulation.

Briefly, the automated cell management system according to the present invention comprises an apparatus comprising: a mechanism for incubating cells comprising an housing having a chamber used to provide controlled environmental conditions in which cells may be cultured and manipulated (such chamber may also be referred to as a "biochamber"); a storage array (rack system) for accommodating a plurality of cell culture devices, wherein a cell culture device comprises a housing (preferably a frame) to which is secured (by a leak-proof sealing) at least one gas permeable, liquid impermeable membrane in forming one or more chambers for culturing cells (e.g., a cell culture device comprises one or more chambers for culturing cells, and at least one gas permeable, liquid impermeable membrane forms at least one surface (wall) of the chamber to permit transfer of gases in and out of the chamber, and wherein an opposing wall may comprise a second membrane or a rigid plastic surface or a combination thereof); a loading station for introducing cell culture devices into the biochamber, and more preferably, for introducing cell culture devices into the storage array contained within the biochamber; a handling device which comprises a mechanism for moving one or more cell culture devices within the biochamber (e.g., to a specific desired position in the interior of the biochamber); a means for harvesting a cell culture component from a cell culture device, wherein the cell culture component comprises cultured cells, cell culture medium, or a combination thereof; and one or more processing stations. A processing station is capable of performing a process selected from the group consisting of aspirating a substance from a cell culture device, injecting a substance into the cell culture device, or a combination thereof (e.g., can perform both operations of aspirating and injecting); wherein, preferably, a substance comprises tissue culture medium, cell culture medium, cells, one or more biological substances, one or more reagents, or a combination thereof. The automated cell management system may further comprise one or more components selected from the group consisting of: a centrifuge for centrifuging one or more cell culture devices; a mechanism for tracking (e.g., one or more of locating or identifying or cataloging) a cell culture device in relation to (e.g., for loading into, or within the biochamber of, or discharged from, or a combination thereof) the automated cell management system; a plurality of reservoirs which are in fluid communication with a station selected from the group consisting of one or more processing stations, one or more evaluation stations, and a combination thereof; a discharge station for permitting removal of cell culture devices from the automated cell management system, and more preferably, into which is delivered cell culture devices unloaded from the storage array for subsequent removal from the automated cell management system; a microprocessor for controlling functions and programmable operations of the automated cell management system, and which may further process and store data generated by the functions and programmable operations of the automated cell management system; one or more evaluation stations for measuring one or more cell culture parameters; one or more means for sterilization of components and surfaces within the biochamber; or a combination thereof.

These and other objects and advantages of the invention will become more apparent from the following detailed description taken in conjunction with the accompanying drawings.

BRIEF DESCRIPTION OF THE DRAWINGS

FIG. 6A is an exploded perspective view of a centrifuge for use in centrifuging a cell culture device.

FIG. 6B is another exploded perspective view of a centrifuge for use in centrifuging a cell culture device.

FIG. 6C is an exploded perspective view, with a cross-section for viewing purposes, of another embodiment of a centrifuge for use in centrifuging a cell culture device.

FIG. 6D is an exploded perspective view, with a cross-section for viewing purposes, of another embodiment of a centrifuge for use in centrifuging a cell culture device.

FIG. 6E is an exploded perspective view of an embodiment of an upper cover plate comprising a component of a centrifuge illustrated in FIG. 6A.

FIG. 6F is an exploded perspective view showing of an embodiment of a support plate comprising a component of a centrifuge illustrated in FIG. 6A, and a cell culture device to be supported in the support plate.

FIG. 6G is an exploded perspective view showing of an embodiment a combination of a upper cover plate, a support plate, and a cell culture device.

FIG. 8 shows a block diagram of a microprocessor in a preferred embodiment of the automated cell management system.

DETAILED DESCRIPTION OF THE INVENTION

Definitions

Figure 1:
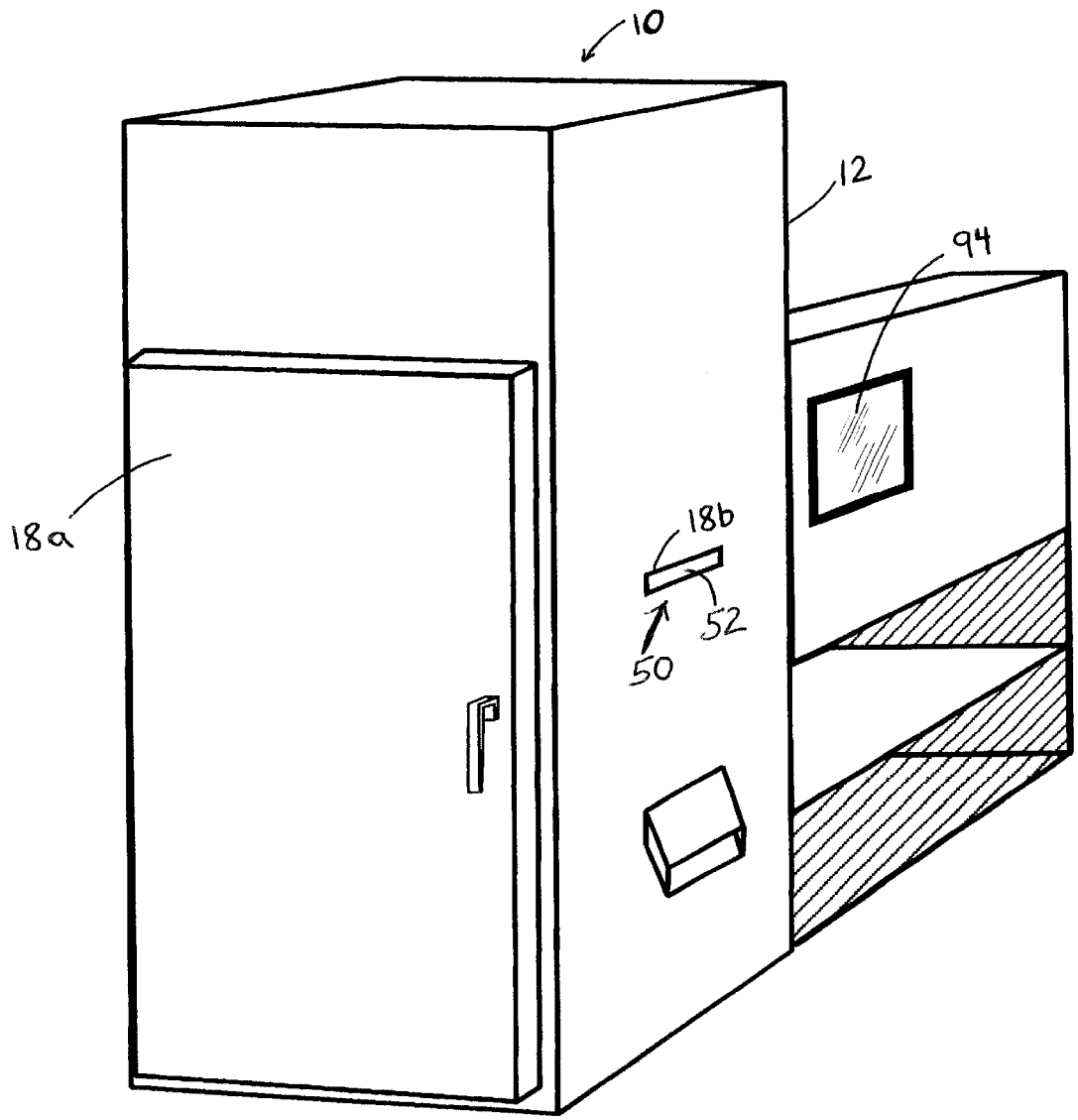
FIG. 1 is a perspective view of an embodiment of an automated cell management system according to the present invention.

The term "tissue culture medium" is used herein, for the purposes of the specification and claims, to mean a liquid solution which is used to provide sufficient nutrients (e.g., vitamins, amino acids, essential nutrients, salts, and the like) and properties (e.g., osmolarity, buffering) to maintain living cells (or living cells in a tissue) and support their growth. Commercially available tissue culture medium is known to those skilled in the art. The term "cell culture medium" is used herein, for the purposes of the specification and claims, to mean tissue culture medium that has been incubated with cultured cells in forming a cell culture; and more preferably refers to tissue culture medium that further comprises substances secreted, excreted or released by cultured cells, or other compositional and/or physical changes that occur in the medium resulting from culturing the cells in the presence of the tissue culture medium.

Note in describing embodiments of the present invention, such terms as "first", "second", "lower", "upper", and the like are words of convenience in order to distinguish between different elements. Such terms are not intended to be limiting as to the sequence of a method or priority in which the different elements may be utilized.

The automated cell management system according to the present invention is provided for high-throughput cell culture and for performing operations of cell culturing and cell culture manipulation. It will be apparent to one skilled in the art that cells which may be cultured in the automated cell management system comprise one or more cell types including, but not limited to, animal cells, insect cells, mammalian cells, human cells, transgenic cells, genetically engineered cells, transformed cells, cell lines, plant cells, anchorage-dependent cells, anchorage-independent cells, and other cells capable of being cultured in vitro as known in the art. The automated cell management system accommodates a plurality of cell culture devices wherein each cell culture device is comprised of a housing (preferably a frame) to which is secured (e.g., by a leak-proof sealing) at least one gas permeable, liquid impermeable membrane in forming a cell culture chamber. A preferred cell culture device for use in the automated cell management system according to the present invention is described in more detail in co-pending U.S. application Ser. Nos. 09/526,006, 09/724,153, 09/724,251, and 09/855,920 (the disclosures of which are herein incorporated by reference). The cell culture device may have one culture chamber or may comprise a plurality of culture (multi-) chambers. Preferably, a cell culture device has a number of culture chambers ranging from 1 to about 96; and more preferably, from 1 to about 8. In a preferred embodiment, two liquid impermeable membranes are secured to a frame in forming opposing walls of the cell culture chamber, wherein at least one of the membranes is gas permeable; and more preferably, both membranes are gas permeable. In an alternative embodiment, there is one gas permeable, liquid impermeable membrane secured to the frame with the opposing surface comprising a rigid, clear plastic material typical of conventional cell culture containers (e.g., tissue culture flask and petri dish). The gas permeable membrane is capable of allowing transfer of gases into and out of the culture chamber, and preferably is optically transparent and clear for permitting observation of the cell culture. The at least one gas permeable membrane may be secured to the frame in a leak-proof sealing using a mechanical means (e.g., heat bonding, ultrasonic welding, pressure fit sealing, or a molding process), or a chemical means (e.g., an adhesive).

The housing (preferably a frame) of the cell culture device may be of a basic biocompatible composition that may comprise suitable plastic, thermoplastic, synthetic, or natural materials which can be fabricated into a framework structure, thereby achieving the required structural integrity for its intended purpose. Relative to the mechanism for tracking each cell culture device in the automated cell management system according to the present invention, in a preferred embodiment the housing, and preferably the frame, of the cell culture device further comprises an identification code. An identification code comprises an identifier placed on or made a part of a frame, and which may include, but is not limited to, a bar code, a number, a series of numbers, a color, a series of colors, a letter, a series of letters, a symbol, a series of symbols, and a combination thereof. The identification code may be used for tracking (e.g., one or more of locating, identifying, identifying the position of as relative to a point of origin, or cataloging (keeping a record of)) the cell culture device, bearing that identification code which is being tracked, within or relative to (e.g., to be loaded into and/or that has been discarded from) the automated cell management system. While the identification code can appear anywhere on the frame, preferably the identification code is accessible for reading by a reader means, as will be more apparent from the following descriptions. Preferably, the identification code of each cell culture device in the automated cell management system is unique to the cell culture device bearing the identification code, thereby allowing each cell culture device in the automated cell management system to be distinguished from any other cell culture device in the automated cell management system.

The culture chamber of the cell culture device, such as formed by the frame and two parallel, spaced apart membranes (or a membrane and an opposing rigid surface as previously described herein), is accessed by at least one access port which extends between (in forming a passageway between) the outer surface of the frame and the chamber. Preferably, the at least one access port is resealable, and serves as a means by which substances can be introduced into (e.g., cells and/or tissue culture medium) or withdrawn from (e.g., cells and/or cell culture medium) the culture chamber while maintaining the culture chamber of the cell culture device as sterile. In a preferred embodiment, the at least one access port comprises two access ports appearing on the same side of the cell culture device, with each access port being sealed by a septum which comprises an elastomeric material that fills all or a substantial portion of the access port, and which is sufficiently pliable to be self-sealing; e.g., thereby allowing for penetration by a tip, and resealing to a leak proof seal after tip withdrawal. The elastomeric material may further comprise an antimicrobial agent (e.g., triclosan or 5-chloro-2-(2,4-dichloro-phenoxy) phenol) incorporated therein to form a surface coating on the septum.

In a preferred embodiment, the cell culture device is generally rectangular, and generally flat; e.g., similar to the form of a cassette. In a more preferred embodiment, the cell culture device has a length in a range of from about 10 cm to about 13.5 cm, a width in a range of from about 7 cm to about 9 cm, and a height in a range of from about 0.2 cm to about 1.0 cm. In a more preferred embodiment, the cell culture device has a length of about 12.7 cm, a width of about 8.5 cm, and a height of about 0.58 cm. Although there is no general relative restriction on either the shape or size of the culture chamber, in a preferred embodiment for culturing to achieve a high density of cells, the average distance between the two membranes which form the chamber is in a range of from about 0.05 to about 0.4 inches, and more preferably is in the range of from about 0.07 to about 0.08 inches.

Figure 2:
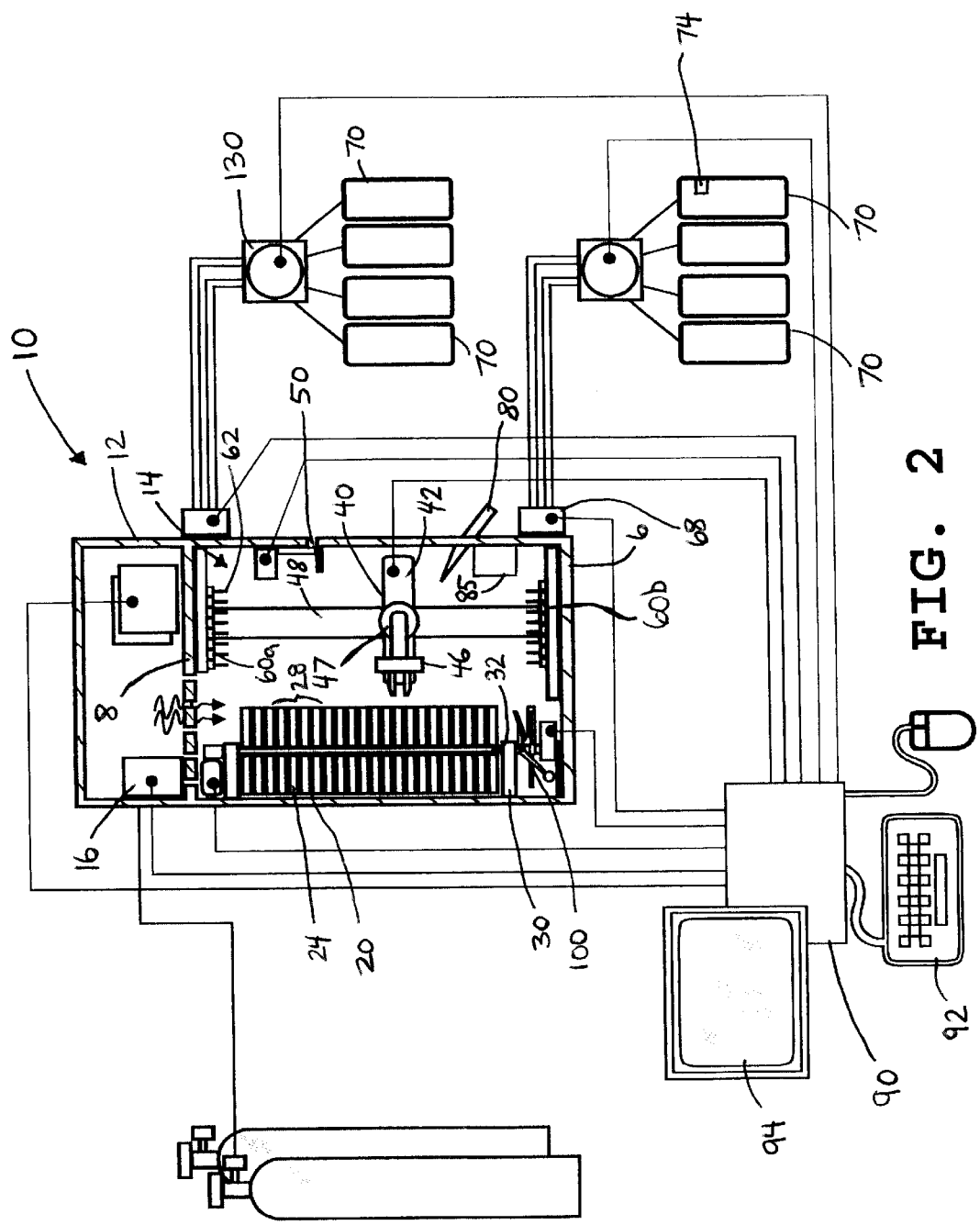
FIG. 2 is a schematic representation of components, with a cross-section for viewing purposes, of an embodiment of an automated cell management system.

An automated cell management system 10, in accordance with the present invention and as shown in FIGS. 1 & 2, comprises a housing 12 having walls, and a biochamber 14 for providing a controlled environment particularly suited for culturing cells. Housing 12 may comprise isotherm walls forming a biochamber 14, and an environment controlling mechanism 16 for controlling the environmental conditions of biochamber 14. Housing 12 has one or more sealable accesses 18. In one preferred embodiment, at least one access 18 comprises a securable, sealable panel or door which is openable to access biochamber 14, and closable to form a closed environment within biochamber 14. In another preferred embodiment, the securable, sealable panel comprises a transparent (e.g., glass, or a clear synthetic resin such as plexiglass) panel which is sealingly engaged with housing 12 in hermetically sealing biochamber 14, for permitting a user to view (visually) the biochamber from outside the apparatus comprising the automated management system without breaching the biochamber environment. Environment controlling mechanism 16 controls the environment conditions in biochamber 14 in which cells may be cultured and manipulated by controlling a parameter selected from the group consisting of temperature, atmospheric gas content (e.g., $CO_2$, $O_2$), humidity (e.g., water vapor content), pressure, airflow, and a combination thereof. Preferably, environment controlling mechanism 16 includes, but is not limited to, a heating mechanism, a humidity control mechanism, a $CO_2$ controller (e.g., $CO_2$ tank, valve, and sensor); and may further comprise a controlling pressure/airflow mechanism preferably including a pressure pump means or blower means (e.g., preferably, for providing a laminar flow of filtered air), and may further comprise a pressure relief fitting, and a pressure relief valve; such as by using standard components of typical tissue culture incubators as known to those skilled in the art of cell culture. As apparent to one skilled in the art, desired environmental conditions for culturing cells (hence, in biochamber 14) include maintenance at a desired temperature in the range of about 35° C. to about 42° C., and more preferably about 37° C.; and may further comprise a $CO_2$ content in a range of from about 1% to about 15%; and may further comprise an $O_2$ content in a range of from about 1% to about 20%. In normal operation, environmental controlling mechanism 16 is controlled by a microprocessor by which operations may be programmed in providing controlled environment conditions for the cultured cells housed in biochamber 14 of automated cell management system 10.

Figure 3:
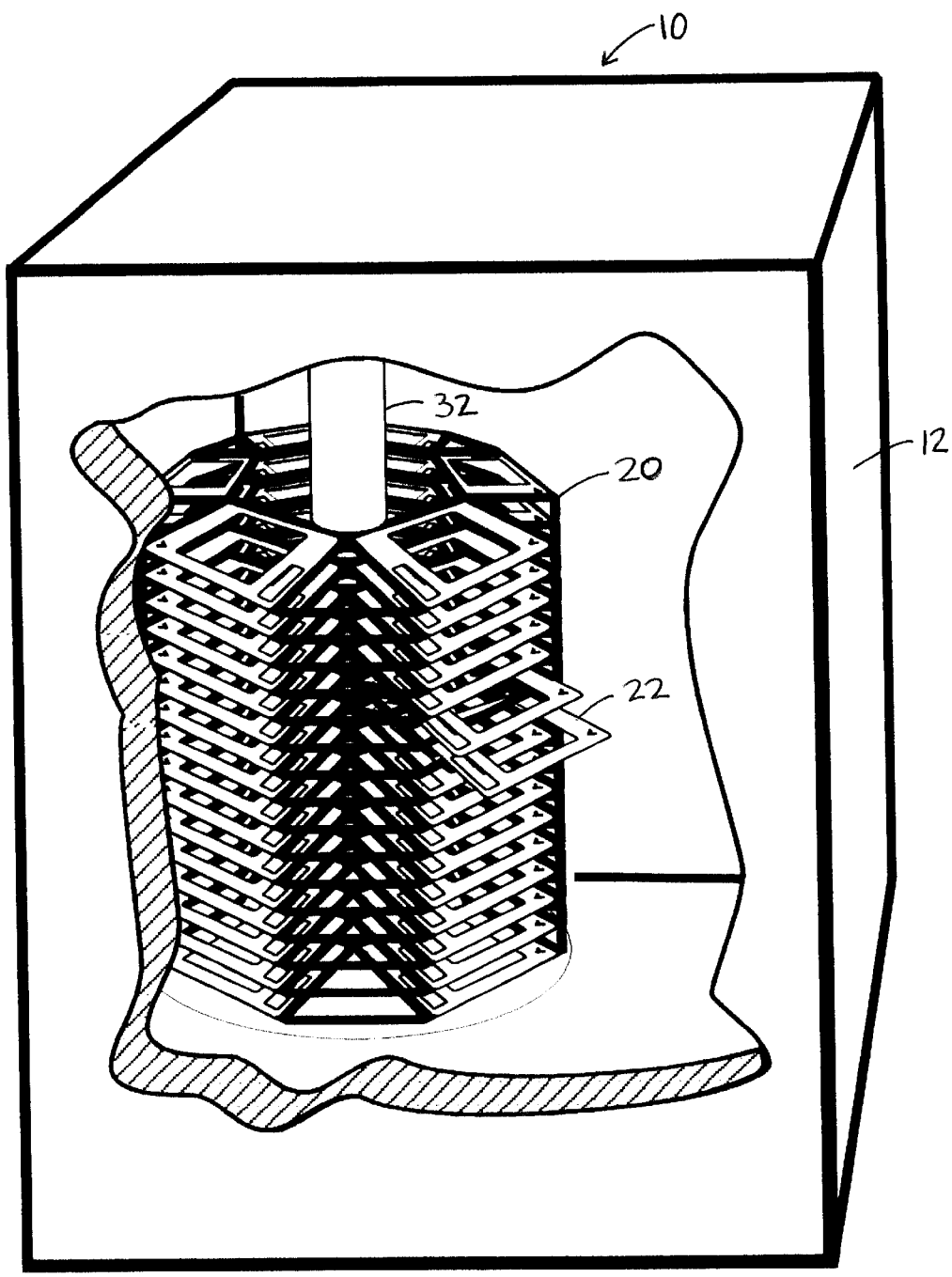
FIG. 3 is an exploded perspective view of an embodiment of a storage array for holding a plurality of cell culture devices.

With reference to FIGS. 2 & 3, contained within biochamber 14 of automated cell management system 10, is storage array 20 for storing a number of cell culture devices 22. While the storage array may be adapted to hold as few as 10 cell culture devices and as many as over 1,000 cell culture devices, preferably the number of cell culture devices which can be stored in the storage array is a number comprising at least 50 cell culture devices, and the number comprising no more than 1,000 cell culture devices; and more preferably, the number comprising at least 300 cell culture devices and the number comprising no more than 500 devices; in providing high-throughput cell culture using the automated cell management system according to the present invention. While the cell culture devices may be stored in one of a number of spatial arrangements, in a preferred embodiment, and as shown in FIG. 3, each cell culture device 22 is stored generally horizontally in storage array 20. In a preferred embodiment, storage array 20 comprises a plurality of positions 24, wherein each position 24 is a passageway defined in storage array 20, adapted to securely receive and hold a cell culture device 22, and which allows a cell culture device to be loaded into, or removed from, storage array 20. Preferably, each position 24, of the plurality of positions of the storage array, comprises a coordinate representative of that position for distinguishing between each position of the plurality of positions. In that regard, each cell culture device 22 is stored in a separate position 24 (e.g., slot or tray) of the storage array 20, wherein each position can further comprise a coordinate for tracking that particular cell culture device in the automated cell management system. Thus, in one embodiment, a mechanism for tracking a cell culture device comprises recording (e.g., entering and storing data related to) such coordinates (e.g., in a written log of coordinates or by using a computer to log the coordinates), and using the coordinates to track a particular cell culture device by its position 24 in the storage array (in corresponding the position, in which a predetermined cell culture device is located, to a coordinate representative of that position). The coordinates may be generated by any one of several methods known in the art. For example, and as described herein in more detail, a mechanism for tracking cell culture devices 120 may comprise one or more position sensors, placed in the biochamber, that may be used to correlate a specific coordinate with a specific position within the biochamber or relative to the automated cell management system.

The storage array may comprise a capability selected from the group consisting of non-rotatable around its axis, rotatable around its axis, and a combination thereof (e.g., can be locked into place so it is non-rotatable around its axis, but can be unlocked to be rotatable around its axis). In a preferred embodiment in which the storage array is capable of rotating around its axis, and as illustrated in FIG. 2, storage array 20 is mounted in operative connection with one or more rotating means 30. For example, and as apparent to one skilled in the art, the rotating means may comprise an arm with one end operatively connected to a drive motor, and the opposing end being detachably engaged with the storage array in enabling the storage array to be rotated in a back and forth motion. The one or more rotating means may further comprise additional components known to those skilled in the art for achieving rotation and stoppage of rotation of storage array 20 (e.g., microswitches, and the like). For example, a plurality of microswitches may be located adjacent to the drive motor, wherein the microswitches are operated through signals fed from the microprocessor in producing a signal to control and drive the drive motor so as to produce the desired mode (e.g., rotation, locking to be non-rotatable when not rotating). Thus, in a preferred embodiment wherein the storage array is rotatable, the storage array may be in a mode selected from the group consisting of in a non-rotating position, or rotating partial revolutions about its axis (e.g., relative to central drive shaft 32 in a controlled movement in a process selected from the group consisting of "repositioning" such as during a loading process, or "agitation", as known to those skilled in the art). Regarding partial revolutions, in one embodiment storage array 20 may be rotated about its axis to a degree selected in the range from about 10° to about 95°. This allows a vertical arrangement 28 of positions 24 to be shifted (in repositioning the storage array) relative to the degree of rotation. Thus, a series of shifts may be useful in one or more of loading cell culture devices into, or removing cell culture devices from storage array 20. For example, partial revolutions may be utilized in loading the storage array with cell culture devices (e.g., loading one column at a time, then rotating to the next column of the storage array). In another embodiment regarding partial revolutions, storage array 20 may be rotated in a first direction about its axis to a degree selected in the range from about 15° to about 65°, and then rotated back, in a second direction counter to the first direction, about its axis to a degree selected in the range from about 15° to about 65°; thereby resulting in a back and forth motion. As apparent to one skilled in the art, the resultant back and forth motion comprises an agitation of the one or more substances contained in the one or more cell culture devices being agitated (hence, agitates the cell culture components in a culture chamber); and thus, can comprise a mixing process to mix contents of cell culture devices being stored in the storage array when agitated. In a preferred embodiment, a microprocessor controls the operation of the storage array, and more particularly the mode in which the storage array is operating.

Figure 4A:
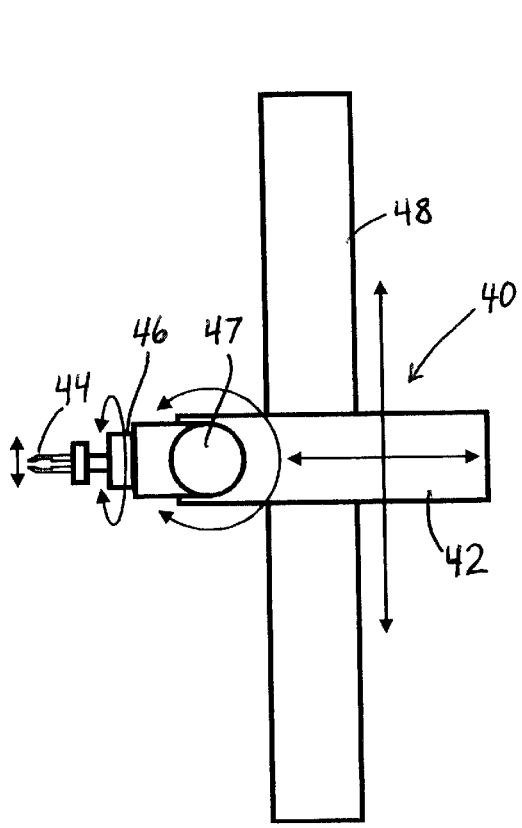
FIG. 4A is an exploded diagrammatic view of an embodiment of a handling device adapted for gripping and moving a cell culture device.
Figure 4B:
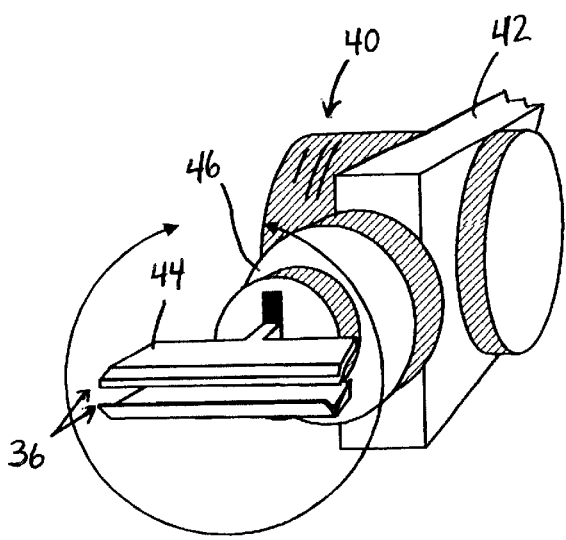
FIG. 4B is an exploded perspective view of a mechanical gripper of the handling device illustrated in FIG. 4A.

With reference to FIGS. 2 & 4A and 4B, contained within biochamber 14 of automated cell management system 10, is handling device 40 for releasably gripping one or more cell culture devices 22, and which facilitates handling of the one or more cell culture devices (e.g., such as by lifting, lowering, tilting, or raising the cell culture device), and also moving the one or more cell culture devices from one location to another within biochamber 14. From one location to another may include, but is not limited to, from a loading station to a storage array, from a storage array to a processing station, from a storage array to a centrifuge, from a centrifuge to the storage array, from a centrifuge to a processing station, from a processing station to a centrifuge, from a storage array to an evaluation station, from a storage array to a discharge station, from a processing station to an evaluation station, from a processing station to a storage array, from a processing station to a discharge station, from an evaluation station to a storage array, from an evaluation station to a processing station, from an evaluation station to a discharge station, and a combination thereof. In a preferred embodiment, the handling device releasably grips a single cell culture device. Preferably, handling device 40 may be used to rapidly locate, with precision, a cell culture device 22 within biochamber 14 of automated cell management system 10. As shown in FIGS. 2, 4A, & 4B, in a preferred embodiment, handling device 40 comprises a device typically known to those skilled in the art as a mechanical gripper. For example, handling device 40 comprises a mechanical arm 42 coupled to a mechanical gripper 44. Mechanical arm 42 is for positioning mechanical gripper 44 (e.g., with respect to a cell culture device and/or with respect to a defined location within chamber 14), and mechanical gripper 44 is for releasably gripping a cell culture device in a process of moving a cell culture device from one location to another. Mechanical gripper 44 is mounted at one end of mechanical arm 42 and the opposite end of mechanical arm 42 is secured (e.g., via a base unit 48 which is mounted) to a surface of the automated cell management system. With regard to a base unit, the base unit may further comprise one or more tracks, in which the mechanical arm may be moved (see, e.g., vertical arrows in FIG. 4A), in allowing the handling device to reach various locations within the biochamber of the automated cell management system. In a preferred embodiment, the handling device comprises a pivot point 46, formed where mechanical gripper 44 joins mechanical arm 42, in forming a translational joint that allows mechanical gripper 44 to be rotated in one or more planes with respect to mechanical arm 42 (see, e.g., arrows in FIG. 4B). Preferably, handling device 40 comprises a second pivot point 47 which is located on mechanical arm 42 (e.g., an arm pin) in forming a translational arm joint that allows mechanical gripper to be rotated in directions perpendicular (see, e.g., arrows around pivot point 47 as illustrated in FIG. 4A) to the rotational movement allowed by pivot point 46. By virtue of these translational joints, positioning of mechanical gripper, and its ability to tilt a gripped cell culture device in one or more planes with respect thereto, is very flexible and adaptable. Mechanical gripper 44 further comprises a means for releasably gripping a cell culture device. As apparent to one skilled in the art from the descriptions herein, a means for releasably gripping includes, but is not limited to, jaws which are controlled to open and close around the edge of the cell culture device in releasably gripping the cell culture device; or multiple vacuum ports through which a vacuum is applied to hold the gripped cell culture device in contact with the mechanical gripper, and wherein the vacuum may be discontinued when the cell culture device is to be released from the mechanical gripper. In a preferred embodiment, and as illustrated in FIG. 4B, mechanical gripper is opened a distance 36 sufficient to fit around an edge of the cell culture device, and then may be closed to releasably grip the cell culture device. The operation (e.g., with respect to one or more of movement between locations, releasably gripping a cell culture device, and rotational movements) of handling device 40 may be controlled by a microprocessor.

Automated cell management system 10 further comprises a loading station for introducing cell culture devices into the biochamber, and more preferably, for introducing cell culture devices into the storage array. In one embodiment, loading of the storage array with cell culture devices is performed manually. Thus, in this embodiment, the loading station comprises an access 18a (comprising a securable, sealable panel or door) which is openable to access biochamber 14. Cell culture devices may then be manually loaded into the storage array by placing each cell culture device in a separate position 24 of the storage array. After manually loading the storage array, access 18 may then be closed to form a closed environment for biochamber 14. At the option of the user, the user then may manually enter into a microprocessor the specific position of the storage array into which a specific cell culture device was inserted, in tracking each cell culture device that was loaded into the storage array.

Alternatively, and in a more preferred embodiment, loading of the storage array with cell culture devices is performed automatically. In that regard, and as shown in FIG. 1, loading station 50 comprises access 18b, comprising a sealable slot 52 for receiving and through which is fed cell culture devices in a loading process, preferably operatively connected to infeed conveyor (preferably an infeed conveyor which is motorized for feeding cell culture devices through the access in a loading process). As will be evident to those skilled in the art, one or more suitable drive motors and linkages can be operatively connected to the infeed conveyor infeed conveyor) for driving the conveyor in a conventional manner; and that the operation of the infeed conveyor (via programmable control over the drive motor (s)) may be controlled by the microprocessor of the automated cell management system. As a cell culture device is placed one at a time into loading station 50, the cell culture device is then fed into biochamber 14 and gripped by handling device 40, wherein handling device 40 then places the cell culture device in a separate position 24 of the storage array 20. In one embodiment, position sensors, operatively connected to handling device 40, may be used to send data to a microprocessor as to the specific position of the storage array into which a specific cell culture device was inserted, in tracking each cell culture device that was loaded into the storage array. Tracking of a particular cell culture device that is introduced into the automated cell management system may further comprise use, and data entry and storage into the microprocessor, of the identification code unique for each cell culture device that is loaded.

Figure 5:
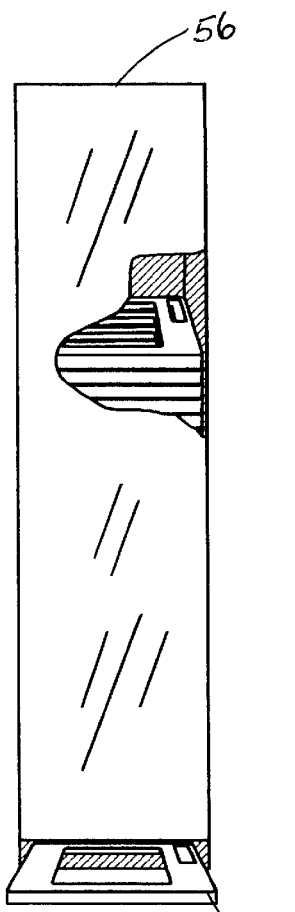
FIG. 5 is a perspective view, with a cross-section for viewing purposes, of an embodiment of a loading cassette for introducing cell culture devices into the loading station.

In a more preferred embodiment, loading station 50 further comprises a loading cassette 56 containing a plurality of cell culture devices stacked vertically (one on top of each other; as illustrated in FIG. 5). Loading cassette 56 may be operatively connected to loading station 50 so that the loading cassette places the cell culture devices, one at a time, in a loading process. An infeed conveyor of the loading station may programmed at a predetermined speed for feeding a cell culture device into biochamber 14 at a constant interval which is a sufficient length of time for the handling device to receive a cell culture device from the infeed conveyor, load the cell culture device into the storage array, and return back to the infeed conveyor to receive the next cell device to be loaded. As a cell culture device is pulled from the bottom of loading cassette 56 and fed along infeed conveyor 54 into biochamber 14, the next cell culture device, in sequential order in the vertical stack of cell culture devices contained in the loading cassette, drops down in position to be engaged by and fed along the infeed conveyor 54 in loading the cell culture device into the automated cell management system 10. It will be appreciated by those skilled in the art that the dimensions of the infeed conveyor and the loading cassette for loading cell culture devices can be proportionately expanded or decreased in size depending on the desired size of the cell culture devices being loaded and stacked, as well as the desired number of cell culture devices to be loaded.

Automated cell management system 10 may further comprise a centrifuge 100 for centrifuging one or more cell culture devices positioned in the centrifuge so as to pellet cultured cells contained in the one or more cell culture devices. By centrifugal force, cultured cells may be pelleted in a specific location (e.g., the location depending on how a cell culture device is loaded within the storage array) within a cell culture device, thereby allowing for cell culture medium to be removed from the cell culture device containing the pelleted cells. More specifically, a cell culture device, having a cell culture chamber containing cultured cells (whether anchorage-dependent or anchorage-independent cells) and culture medium (or other suitable fluid), is held in a fixed position in the centrifuge. The centrifuge is accelerated to a predetermined rotational speed causing centrifugal forces to pellet cells to a surface (preferably, an inside edge) of the chamber of the cell culture device, thereby allowing the culture medium (or other suitable fluid) to be aspirated from the cell culture device while allowing the cells to remain as a pellet within the cell culture device. The rotational speed, and the length of time of centrifugation, may be controlled by a microprocessor. The rotational speed necessary to pellet cells is generally dependent on the type of centrifuge, the cell culture device, and other factors known in the art. In a preferred embodiment, the rotational speed may be a speed selected in a range of from about 1,000 revolutions per minute (rpm) to about 2,000 rpm; and the length of time of centrifugation may be a time selected in a range of from about 5 minutes to about 20 minutes.

As apparent to one skilled in the art, a number of conventional centrifuge types may be used to centrifuge one or more cell culture devices contained in the automated cell management system according to the present invention. For example, a swinging bucket-type centrifuge may be housed in the biochamber of automated cell management system. Into the swinging bucket rotor may be placed one or more cell culture devices for centrifugation. A cell culture device is held into position by either a centrifuge bucket adapted to receive and support the cell culture device, or an adaptor adapted to receive and support the cell culture device wherein the adaptor is contained within a centrifuge bucket (as described in more detail in co-pending U.S. application Ser. No. 09/861,686, the disclosure of which is herein incorporated by reference). The one or more cell culture devices placed in the swinging bucket rotor are then centrifuged. In a more preferred embodiment, as illustrated in FIGS. 6A–D, centrifuge 100 comprises conventional components (e.g., drive motor, and the like) including a rotatable shaft 102. Fixedly secured to shaft 102 are radially extending arms comprising support plate 104 and upper cover plate 106. As shown in FIGS. 6E–G, support plate 104 may be dimensioned to securely receive a cell culture device 22. After loading cell culture device 22 into support plate 104 (as diagrammatically illustrated in FIG. 6F), upper cover plate may then be positioned so as to contact the cell culture device, on the side opposite that contacting the support plate) so that the cell culture device is sandwiched and secured between support plate 104 and upper cover plate 106 (see, e.g., FIG. 6G). As apparent to one skilled in the art, the upper cover plate and support plate may be positioned on opposite sides of the cell culture device, and then secure the cell culture device therebetween using methods standard in the art (e.g., a spring-loaded mechanism, or mechanism employing one or more screws or bolts which are then threadingly engaged). In a preferred embodiment, upper cover plate comprises weight 108 which serves (a) to close upper cover plate by the movement of weight 108 outwardly in response to applied centrifugal forces in causing the upper cover plate to contact the cell culture device (as shown in FIG. 6B), and (b) to even the load (e.g., wherein the heaviness of the weight is equal to or substantially equal to the heaviness of the cell culture device and the portions of the upper cover plate and support plate in contact therewith) so that the centrifuge may remain balanced during its rotation. In another preferred embodiment, as illustrated in FIGS. 6C & 6D, centrifuge 100 may further comprise a two part housing 110 formed of an upper cover 111 and lower cover 112 as conventional in the art. The two part housing 110 may be closed, by contacting and securing upper cover 111 and lower cover 112 together using means standard in the art, in providing a sealed environment in which a cell culture device may be centrifuged (see, e.g., FIG. 6D).

Automated cell management system 10 may further comprise a means for harvesting, from a cell culture device, a cell culture component comprised of one or more of cultured cells or cell culture medium. Harvesting is herein defined, for purposes of the specification and claims, to mean collection of the cell culture component from the cell culture device, and may further comprise separation between cell culture medium and cultured cells, as achieved within the automated cell management system according to the present invention. In one embodiment, harvesting is accomplished using a combination comprising handling device 40, and one or more processing stations. For example, a cell culture device may be moved by the handling device to a processing station where cell culture medium may be harvested from a cell culture device containing anchorage-dependent cells by aspirating cell culture medium out of the cell culture device. In another example, anchorage-independent, cultured cells and cell culture medium may be harvested from a cell culture device containing anchorage-independent cells by aspirating both the cells and cell culture medium out of the cell culture device at a processing station.

In another embodiment, harvesting may be accomplished using a combination comprising centrifuge 100, handling device 40, and one or more processing stations. More particularly, harvesting may comprise a process of centrifuging one or more cell culture devices (as described herein in more detail) for separating cultured cells from cell culture medium, and then collecting the desired cell culture component from (e.g., aspirating the cell culture component out of) the centrifuged cell culture device. For example, in harvesting culture medium from a cell culture comprising anchorage-independent cells grown in a cell culture device, the cell culture device is centrifuged in the centrifuge in pelleting the cultured cells by centrifugation. The handling device may then be maneuvered to remove the cell culture device from the centrifuge, and move the centrifuged cell culture device to a processing station where the cell culture medium may be removed by aspiration from the culture chamber of the cell culture device in harvesting the cell culture medium. The pelleted cells may also be harvested by injecting a fluid into the cell culture device in contacting the cells and resuspending the cells in the fluid in forming a cell suspension, and then aspirating the cell suspension from the cell culture device in harvesting a cell culture component comprising the cultured cells.

Harvesting as related to anchorage-dependent cells grown in a cell culture device, may be achieved in one of several ways. In one embodiment, to harvest the anchorage-dependent cultured cells anchored to the growth surface of the cell culture device, the cells need to be loosened from the growth surface so that the cells become detached from the growth surface. One method to detach anchorage-dependent cells from adhering to a growth surface comprising a membrane is to pellet the cells by centrifugation of the cell culture device containing the cultured cells in a centrifuge. More specifically, anchorage-dependent cells may be detached from the membrane surface of a cell culture device by the centrifugal forces encountered during centrifugation. The cell detachment may further be facilitated by contacting the cells with a dissociation reagent (e.g., prior to centrifugation). Dissociation reagents are solutions well known in the art to include, but are not limited to, a solution comprising one or more chelators (ethylenediamine tetraacetate, "EDTA"; ethylene glycol-bis beta-aminoethyl ether N,N,N',N'-tetraacetic acid, "EGTA"; versen; and the like), one or more proteolytic enzymes (e.g., ficin, pepsin, trypsin, chymotrypsin, papain, and the like, with trypsin being a preferred enzyme), or a combination thereof (e.g., a combination of trypsin and EDTA). For centrifugation, the cell culture device is held in a fixed position in the centrifuge, and the rotor is accelerated to a predetermined rotational speed causing centrifugal forces to pellet cells to an edge within the culture chamber of the cell culture device. The cell culture medium and pelleted cells may then be collected by a process described herein in more detail. For example, after centrifugation, the handling device may be maneuvered to remove the cell culture device from the centrifuge, and move the cell culture device to a processing station where the cell culture medium may be removed by aspiration while the cultured cells remain pelleted in the cell culture device. At a processing station, the cell culture device may be further processed by introducing a fluid into the cell culture device to contact and resuspend the pelleted cells in forming a cell suspension, and the cell suspension may then be aspirated out of the cell culture device in harvesting the cultured cells. In an embodiment in which a fluid comprising a dissociation reagent is introduced into the cell culture device so that the fluid contacts the adhered cells, agitation may be provided by the handling device to facilitate loosening of the cells in contact with the fluid. Alternatively, the handling device may move the cell culture device containing the fluid to the storage array wherein the cell culture device is placed securely into the storage array, and the storage array is then rotated in a back and forth motion, thereby agitating the anchorage-dependent cells to loosen from the surface of the cell culture device to which they are adhered. The cell culture device may then be processed by centrifugation or other desired process.

In another embodiment, anchorage-dependent cells may be detached from a membrane of the cell culture device to which they adhere by a process of dilating the elastomeric membrane (e.g., such as by injecting into the cell culture device a substance comprising fluid, air, or a combination thereof), and then removing the substance so that the membrane returns to an undilated form, which causes the cells to loosen their attachment to the membrane surface. The detaching process may further be facilitated by introducing a fluid comprising a dissociation reagent into the cell culture device to contact the anchorage-dependent cells (either before or after the dilation step). For example, a cell culture device contains (a) anchorage-dependent cells adhered to the surface of the membrane, and (b) a fluid in contact with the cells (e.g., cell culture medium or other physiological solution compatible for handling of cultured cells). At a processing station, air is then injected (e.g., in a range of about 2 psi to about 8 psi) into the cell culture device in causing the membranes of the cell culture device to dilate. Thus, for example, where a cell culture device contains 10 ml of fluid in an undilated form, a substance may be introduced in an amount ranging from about 10 ml to about 20 ml to cause dilation of the membrane surface. For example, tips are inserted into the resealable access ports, and air is then introduced through the tips and into the culture chamber. Dilation (wherein the surface of the membrane is stretched or expanded) of the membrane, to which are anchored the anchorage-dependent cells, may cause the cells to loosen and eventually (e.g., typically, within several minutes, depending in the cell type, psi, and other factors) detach from the membrane surface. In particular, after dilating the membrane, the substance (e.g., air) may be aspirated from the culture chamber, and the dilation is then repeated. After repeated dilations, the anchorage-dependent cells become detached and are released into the fluid. Once the cells are loosened (loose attachment or detached), the cell culture device may then be moved to a processing station wherein the cultured cells in solution may be collected by aspiration; or the cell culture device may then be positioned into a centrifuge to pellet the cultured cells by centrifugation. The rotational speed, and the length of time of centrifugation, may be controlled by a microprocessor. If desired, the pelleted cells may be collected. In the collection process, the handling device may remove the cell culture device containing the pelleted cells from the centrifuge, move the cell culture device to a processing station which may be used to inject a fluid (e.g., buffer or tissue culture medium) into the culture chamber of the cell culture device to resuspend the pelleted cells (e.g., resuspension may further be assisted by agitation of the cell culture device) in forming a cell suspension, and then withdrawing (e.g., by aspiration) the cell suspension from the culture chamber of the cell culture device in harvesting the cultured cells.

Automated cell management system 10 further comprises one or more processing stations which may process a cell culture device by performing a function selected from the group consisting of aspirating contents from a cell culture device, introducing (e.g., injecting) a substance into the cell culture device, separating cell culture components, and a combination thereof. A processing station may comprise one or more means for aspirating and dispensing (e.g., syringe, pipette system, micropipette system, and the like). As apparent to one skilled in the art from the descriptions herein, the substance introduced into or aspirated from a cell culture device may include, but is not limited to, a fluid (e.g., a chemical-containing solution, reagent, a physiological solution such as a buffer or balanced salt solution, a wash solution, tissue culture medium, cell culture medium, or the like), cells (e.g., cells to be cultured, cultured cells, or a combination thereof), one or more biological substances, air, or a combination thereof. With reference to FIGS. 2, 7A–D, a processing station 60 comprises a pipette system; and is preferably adapted to receive one or more cell culture devices to facilitate processing. Preferably, the pipette system comprises a plurality of pipettes 62, and more preferably a plurality of pipettes arranged as a row of pairs of pipettes. Preferably, the number of pipettes in a pipette system is in the range of from about 2 to about 500, and more preferably, from about 2 to about 50. In a preferred embodiment, the cell culture device 22 comprises two access ports 26, each sealed by a resealable elastomeric septum, which are spaced apart on the same side (e.g., exterior edge) of the cell culture device. With that arrangement in mind, in a preferred embodiment, each pair of pipettes is spatially arranged such that during the processing operation (e.g., aspirating or injecting) with the pipette system, the tip of a first pipette 62a of the pair is inserted into one access port 26a, and the tip of a second pipette 62b of the pair is inserted into the other access port 26b, of the cell culture device (as aligned and represented in FIG. 7A). It will be apparent to one skilled in the art that the tips of the pair of pipettes may be inserted simultaneously, or substantially at the same time, into the cell culture device being processed. Additionally, it may be preferable that the pipettes be spatially arranged to facilitate loading a multiwell plate or multichamber device (in any arrangement on any multi-well plate format or foot-print as known in the art) with contents harvested from one or more cell culture devices at the processing station (e.g., cells for cell cloning). In that regard, the multwell plate or multichamber device may be held at the processing station by the handling device.

In a preferred embodiment, as illustrated in FIG. 2, a processing station 60 may further comprise a plurality of pumps 130, with each pump being driven by a motor (e.g., stepper motor) that may be controlled by a controller and a microprocessor for regulating the amount of aspiration or injection (dispensing) mediated by each pipette of the system; and may further comprise a plurality of reservoirs 70 in fluid communication with processing station 60. More preferably, each pipette 62 of processing station 60 may be in fluid communication with a reservoir 70, via a fluid pathway (e.g., line or tubing) which allows for the flow of a fluid therethrough, in enabling the flow of fluid between a reservoir and a processing station.

In one embodiment of a processing station, each pipette comprises a pipette tip which may be preferably replaceable for the purpose of avoiding any possible contamination of the pipette from a previous processing operation. Alternatively, the pipette tip may not require replacing as the pipette tip may be washed or otherwise cleaned to avoid any possible contamination of the pipette from a previous processing operation. A preferred wash solution is a physiological solution such as sterile phosphate buffered saline (PBS), although other wash solutions as known to those skilled in the art may be used. When utilizing a wash solution, one or more of the reservoirs of the automated cell management system may be used to store the wash solution for cleaning the pipette system. In the event that there is no risk of contamination of a pipette tip, the step of replacing, washing, or cleaning of the pipette tip may be omitted.

The one or more processing stations 60 are preferably located along, and anchored to for support, one or more walls forming biochamber 14 of automated cell management system 10. In a preferred embodiment, one or more processing stations 60 comprise processing station 60a and processing station 60b. In this preferred embodiment, each of processing stations 60a and 60b comprise a plurality of pipettes arranged as a row of pairs of pipettes, as previously described herein in more detail. Preferably, the row comprises from about 5 to about 25 pairs of pipettes. Preferably, one pipette of a pair is in fluid communication with a reservoir via a fluid pathway; and the other pipette of the pair is operatively connected to a pump wherein the pump can create a vacuum to withdraw air from the culture chamber of a cell culture device accessed by the pipette, or can create an airflow for injecting air into the culture chamber of a cell culture device accessed by the pipette, or can separately perform both operations (creating a vacuum during one processing operation, and creating an airflow during another processing operation).

In a preferred embodiment, and as illustrated in FIG. 2, processing station 60a is mounted to a wall comprising the upper portion of biochamber 14. For example, for illustration, processing station 60a may be affixed to ceiling 8 inside biochamber 14. In a processing operation, handling device 40 moves cell culture device 22 so that its two access ports are accessed by the tips of a pair of pipettes 62a, and 62b. More specifically, handling device 40 moves cell culture device 22 to be aligned and contacted with the pair of pipette tips such that one access port is accessed by pipette 62a, and the other access port is accessed by 62b. This arrangement is particularly useful in a processing operation comprising filling the culture chamber of a cell culture device with a fluid; wherein, before the filling operation, the cell culture chamber of the cell culture device is empty or only partially filled with fluid. More particularly, in this position an air bubble, which forms in the cell culture chamber as it is filled, will be accessible by a first pipette tip. Thus, air may be aspirated through the first pipette tip in contact with an air bubble so as to substantially remove the air (e.g., the air bubble) from the cell culture chamber as it is filled with fluid introduced using a second pipette tip. For purposes of illustration of this point, and in referring to FIG. 7A, pipette 62a and pipette 62b each access a separate access port (e.g., 26a and 26b, respectively) of the cell culture device, wherein air is aspirated from the cell culture device by a vacuum being applied through pipette 62a, and wherein fluid is introduced into the cell culture device by the fluid being pumped through pipette 62b. A processing operation in which a fluid is introduced into a cell culture device includes, but is not limited to, initiation of a cell culture or cell cloning (introduction of cells and a fluid into a cell culture device), addition of tissue culture medium to cells contained in the cell culture device (e.g., to replenish nutrients; i.e., "feeding" the cells as known in the art), addition of a fluid to cells contained in a cell culture device (e.g., during a processing operation comprising protein extraction, nucleic acid molecule extraction, or a combination thereof), addition of one or more biological substance to cells contained in the cell culture device (e.g., cell transfection, cell infection, drug testing), addition of a reagent to into the cell culture device (e.g., a magnetic separation reagent as known in the art such as, but not limited to, a solution comprising magnetic beads coated with an affinity molecule (e.g., antibody), cell staining), and a combination thereof.

Figure 7A:
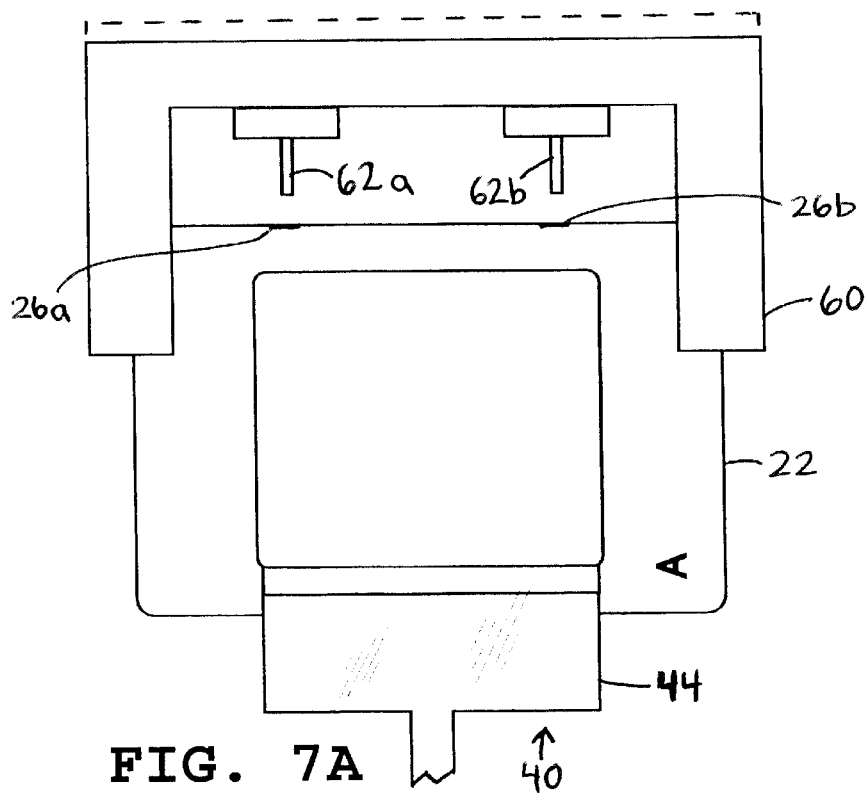
FIG. 7A is an exploded perspective view of an embodiment of a processing station of an automated cell management system according to the present invention.
Figure 7B:
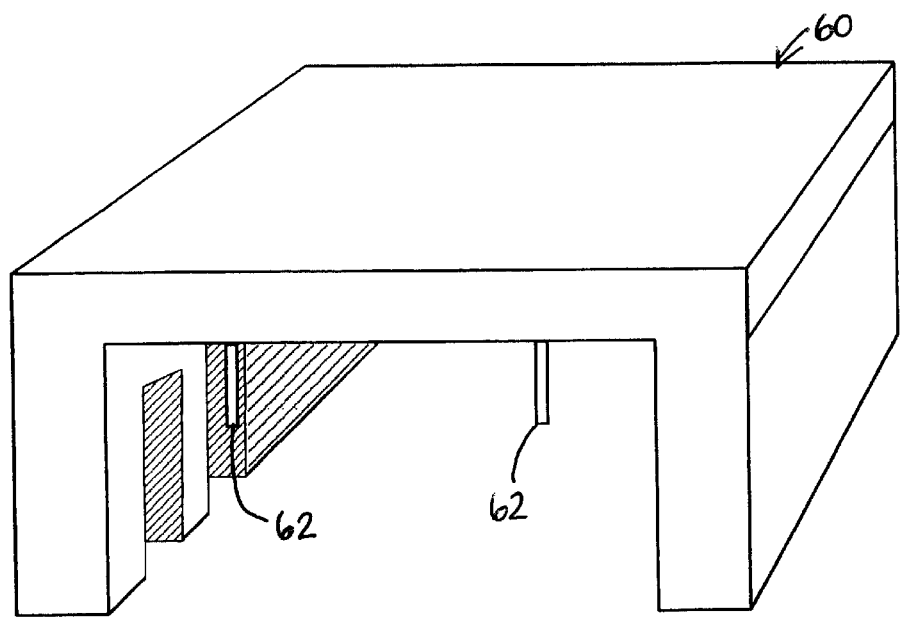
FIG. 7B is an exploded perspective view of an embodiment of a processing station of an automated cell management system according to the present invention.
Figure 7C:
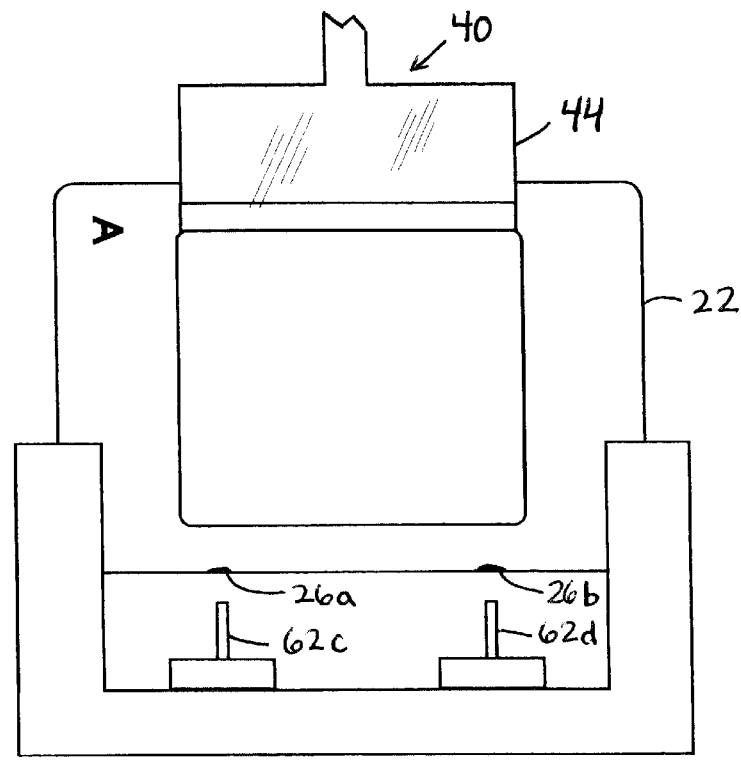
FIG. 7C is an exploded perspective view of an embodiment of a processing station of an automated cell management system according to the present invention.
Figure 7D:
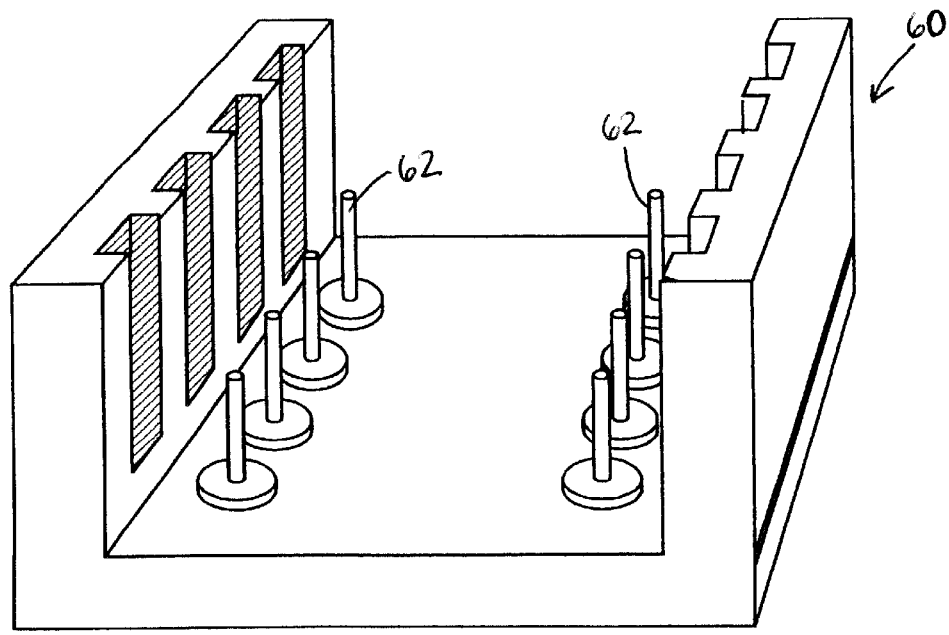
FIG. 7D is an exploded perspective view of an embodiment of a processing station of an automated cell management system according to the present invention.

In a preferred embodiment, and as illustrated in FIG. 2, processing station 60b is mounted to a wall comprising the lower portion of biochamber 14. For example, for illustrative purposes, processing station 60b is affixed to a floor 6 of biochamber 14. As illustrated in FIGS. 7C & D, in a processing operation, handling device 40 moves cell culture device 22 down to and in alignment position with processing station 60 so that the access ports of the cell culture device are accessible by the tips of a pair of pipettes 62c, and 62d. More specifically, handling device 40 moves cell culture device 22 to be aligned and contacted with the pair of pipette tips such that one access port is accessed by pipette 62c, and the other access port is accessed by 62d. This arrangement is particularly useful in a processing operation comprising removing fluid from a cell culture device. For example, emptying the cell culture device may comprise removing all or substantially all of the fluid contained within the culture chamber of the cell culture device. Sampling the cell culture device may comprise removing only a portion of the fluid contained within the culture chamber of the cell culture device. More particularly, in this position, air may be introduced through a first pipette tip into the cell culture chamber as fluid is being removed from the cell culture chamber aspiration using a second pipette tip. When the cell culture device has two opposing membranes forming walls of the cell culture chamber, introducing air into the cell culture chamber as fluid is removed will help to avoid collapse of the membranes. For purposes of illustration of this point, pipette 62c and pipette 62d each access a separate access port (e.g., 26a & 26b, respectively) of the cell culture device, wherein air is introduced into the cell culture device by air being pumped through pipette 62c, and wherein fluid is aspirated from the cell culture device by the fluid being pumped (aspirated) through pipette 62d. A processing operation in which a fluid is withdrawn or otherwise removed from a cell culture device includes, but is not limited to, harvesting, removal of a reagent or wash solution, sampling (e.g., removal of a sample or aliquot of cell culture medium and/or cultured cells for evaluation of one or more cell culture parameters), splitting a cell culture (e.g., removing a portion of the cell culture from one cell culture device for introduction of that portion into one or more additional cell culture devices in seeding/reseeding cell cultures), termination of a cell culture (e.g., removal of cell culture medium and/or cultured cells at a time prior to discharge of a cell culture device), a processing operation comprising protein extraction and/or nucleic acid molecule extraction or magnetic separation, and a combination thereof. As previously described herein in more detail, a processing operation in which air is introduced into the culture chamber of a cell culture device may include, but is not limited to, a sampling operation, or harvesting of anchorage-dependent cells during which air is introduced into the cell culture device to dilate a membrane to which the cells are adhered.

It will be apparent to one skilled in the art that various processing operations, disclosed herein or embodied by the descriptions contained herein, may be used in combination. For purposes of illustration, preferred processing operations performed in the automated cell management system according to the present invention may comprise one or more of: extraction of protein from cultured cells, extraction of protein from culture medium, extraction of nucleic acid molecules from cultured cells, extraction of nucleic acid molecules from cell culture medium, magnetic separation of a desired population of cells cultured in a cell culture device, and staining cells. For example, at the one or more processing stations, proteins may be extracted from the cultured cells or cell culture medium using conventional techniques including, but not limited to, methods utilizing solubility (e.g., solubility in salt solutions, detergent solutions, or solvents), and methods utilizing chromatography (e.g., ion-exchange, affinity, size exclusion, and the like). In one example, a cell culture in a cell culture device is processed for protein extraction in the automated cell management system by: separating the cell culture medium from the cultured cells (e.g., removal of the cell culture medium from the culture chamber of the cell culture device while retaining the cells inside the culture chamber of the cell culture device, as previously described herein in more detail); adding a fluid, comprising a reagent, to the cultured cells under suitable conditions for lysing cells and/or solubilizing proteins from the cultured cells. The processing operation may further comprise centrifuging the cell culture device to pellet whole cells and large debris in providing a supernatant containing proteins extracted from the cultured cells. Examples of reagents and suitable conditions for protein extraction are well known in the art. For example, a reagent for protein extraction typically comprises a buffer (e.g., Tris or Hank's, HEPES, or phosphate buffered saline; in a concentration ranging from about 5 mM to about 0.5 M), one or more detergents (e.g., TWEEN 20, TRITON-X, sodium dodecyl sulfate (SDS), NONIDET P-40, deoxycholate, and the like; in a concentration ranging from about 0.1% to about 5%). The reagent may further comprise one or more protease inhibitors (e.g., aproptenin, leupeptine, pepstatin, PMSF, chymostatin, and the like; e.g., in a concentration ranging from about 1 μg/ml to about 100 μg/ml, or for PMSF, from about 1 mM to about 3 mM). The reagent may further comprise one or more of a salt (e.g., NaCl in a concentration of from about 50 mM to about 200 mM), a chelating agent (e.g., EDTA in a concentration of from about 1 mM to about 50 mM), glycerol, mercaptoethanol, sodium hydroxide (from about 0.1M to about 0.3 M, followed by neutralization with a hydrochloric acid solution), and other additives known in the art for protein extraction. Suitable conditions typically comprise incubating the reagent in contact with the cultured cells (preferably with agitation) for a period ranging from about 10 minutes to about 48 hours, and more preferably for a period ranging from about 30 minutes to about 2 hours.

In another example, a processing operation comprises extraction of nucleic acid molecules from cultured cells or cell culture medium. As apparent to one skilled in the art, nucleic acid molecules may include, but are not limited to, DNA, genomic DNA, plasmid DNA, a DNA vector, RNA, total RNA, mRNA, DNA-RNA hybrid, a combination thereof, and the like. At the one or more processing stations, nucleic acid molecules may be extracted from the cultured cells or culture medium using techniques well known in the art. For example, nucleic acid molecules may be extracted from cultured cells in the cell culture device by contacting the cells with a fluid reagent comprising TRIZOL (a solution of phenol and guanidine isothiocyanate), or other fluid reagent suitable for nucleic acid molecule extraction, using methods known in the art. In one example, a cell culture in a cell culture device is processed for nucleic acid molecule extraction in the automated cell management system by: separating the cell culture medium from the cultured cells (e.g., removal of the cell culture medium from the cell culture device while retaining the cells inside the culture chamber of the cell culture device, as previously described herein in more detail); adding a fluid reagent to the cultured cells under suitable conditions for lysing the cells and for solubilizing nucleic acid molecules from the lysed cells. Suitable conditions typically comprise incubating the fluid reagent in contact with the cultured cells (preferably with agitation) for a period ranging from about 10 minutes to about 24 hours, and more preferably for a period ranging from about 20 minutes to about 1 hour. The resulting lysate comprises solubilized nucleic acid molecules comprising DNA and RNA. DNA and RNA may be purified from the lysate by further processing. For example, the lysate may be harvested from the culture chamber of the cell culture device and flowed to a collection reservoir. The lysate may be removed from the collection reservoir and placed into a centrifuge tube to which chloroform (0.2 ml per ml of TRIZOL) may be added, and then the tube is capped and shaken vigorously. Following centrifugation of the tube (e.g., at 10,000×g for 10 min.), three phases are present: a lower, organic phase containing phenol-chloroform and DNA; an interphase containing DNA; and an upper aqueous phase containing RNA. RNA may be isolated from the upper aqueous phase, and DNA may be isolated from either or both of the lower, organic phase and interphase using methods known in the art (e.g., precipitation).

In another example, a processing operation comprises magnetic separation of a substance to be separated from a cell culture contained in a cell culture device, wherein the substance may comprise a desired population of cells or cell-secreted product (e.g., antibody or cytokines). For example, added to the cell culture device is a magnetic separation reagent comprising magnetic particles coated with a ligand, wherein the ligand has sufficient binding specificity and affinity for the substance desired to be separated and for achieving magnetic separation. After mixing the contents together for a sufficient time for contact and binding interactions to occur between the magnetic separation reagent and the target substance to be separated (in forming complexes), a magnetic sheet may be extended over and contacted with the cell culture device in a face to face manner by which magnetic particles (including those in complexes) are attracted to and held into position (along the inside wall of culture chamber comprising the inner surface of the membrane) by the magnetic field strength of the magnetic sheet. In that regard, the processing station may further comprise one or more magnetic sheets (e.g., plates, pads, or the like) which may be used to contact the cell culture device in a process of magnetic separation. After allowing for a sufficient time for complexes to be held into position along the membrane of the cell culture device, fluid may be removed from the cell culture device by the processing station. In a method of negative selection, the removed fluid is utilized because it comprises one or more desired substances and because the removed fluid has been depleted of other cell culture components. In a process of positive selection, because the substance desired to be separated is held in position by magnetic attraction as complexes in the culture chamber, the removed fluid substantially comprises all of the (unwanted) remainder of the cell culture components. The magnetic sheet may then be removed from the cell culture device in releasing the complexes into the chamber, whereby the complexes may then be aspirated out of the cell culture device by the processing station in separating the substance by magnetic separation.

Automated cell management system 10 may further comprise a mechanism for tracking (e.g., one or more of locating or identifying or cataloging) a cell culture device present in the automated cell management system. In a preferred embodiment, and as previously described herein in more detail, a cell culture device further comprises an identification code which can be used to distinguish it from other cell culture devices present in the automated cell management system, and which may be used for one or more of tracking (e.g., locating or identifying the position of, as relative to a point of origin, the cell culture device, and storing the data related to this function in a microprocessor) the cell culture device having that identification code which is sought to be identified within (e.g., in the biochamber, or in a specific location or position with the biochamber) or relative to (e.g., for loading into, or having been discarded from) the automated cell management system. With a cell culture device having an identification code, a mechanism 120 (as illustrated in FIG. 2) for tracking a cell culture device present in the automated cell management system comprises an identification code reader. Identification code readers are known to those skilled in the art. In a preferred embodiment, the identification code reader may be made a part of the handling device 40, thereby enabling the handling device to read the identification code at any point the cell culture device is moved to, or at a location in the automated cell management system. For example, it may be desirable to read the identification code in moving the cell culture device from the loading station to the storage array, and in moving the cell culture device from the storage array to another location (e.g., a processing station, an evaluation station, a discharge station, centrifuge, and the like). The mechanism for tracking cell culture devices in relation to the apparatus, as exemplified by an identification code reader, may be operatively connected to a microprocessor for purposes which may include, but are not limited to processing and storing of data input with respect to the tracking of cell culture devices. In a preferred embodiment, the identification code comprises a barcode as known to those skilled in the art, and the identification reader comprises a barcode reader as known to those skilled in the art. In another embodiment, and as previously described herein in more detail, each of the various points (e.g., locations) relative to the automated cell management system (e.g., inside the biochamber, inside the automated cell management system, or in a loading cassette outside the automated cell management system) may be assigned a coordinate that comprises a value representing that specific (predetermined) point relative to the automated cell management system. Thus, in another embodiment, a mechanism for tracking cell culture devices comprises entering the coordinates into a microprocessor, wherein software is then programmed to enable a user to utilize a coordinate for tracking a particular cell culture device; and more preferably, enables a handling device to be guided to a specific location in the automated cell management system which is representative of (corresponds to) the coordinate. In another preferred embodiment, the method for tracking cell culture devices in relation to the automated cell management system comprises a combination comprising the identification reader, and the generation of coordinates which are representative of predetermined locations in relation to the automated cell management system.

Automated cell management system 10 may further comprise a plurality of reservoirs 70. Preferably, the plurality of reservoirs are in fluid communication with one or more stations selected from the group consisting of a processing station, an evaluation station, and a combination thereof. The fluid communication may comprise a fluid pathway between a reservoir and one or more stations with which it is in fluid communication (e.g., as diagrammatically represented in FIG. 2). For example, a processing station for introducing a fluid into a cell culture device may be in fluid communication, via a fluid pathway, with one or more reservoirs from which a fluid may be pumped. To illustrate this example, with it being apparent to one skilled in the art that the number of reservoirs and the selection of which fluids are housed therein depends on the preference of a user, a first reservoir may contain tissue culture medium, a second reservoir may contain a wash solution, a third reservoir may contain a buffer, a fourth reservoir may contain a biological substance. Each reservoir has a fluid pathway (e.g., line or tubing that is suitable for its intended purpose as known in the art) that is in fluid communication with the processing station. The fluid flow through the fluid communication between a reservoir and a station may be controlled by a microprocessor. For example, when it is desired to introduce a fluid into a cell culture device, a microprocessor controls a pump to pump the fluid (e.g., tissue culture medium) from a reservoir containing the fluid through a fluid pathway to the processing station in fluid communication with the reservoir, through a pipette, and into the cell culture device. As shown in FIG. 2, processing station 60 may further comprise a set of valves 68 which may be used to regulate the fluid flow of the fluid communication between the reservoir and the processing station. In another example, a processing station for withdrawing a fluid from a cell culture device may be in fluid communication, via a fluid pathway, with one or more reservoirs from which a fluid may be pumped. To illustrate this example, a first reservoir may be for collection of a fluid comprising cell culture medium for further use (e.g., for seeding another culture; or for evaluation), a second reservoir may be a waste container for collection of one or more fluids to be properly discarded (e.g., cell culture medium, wash solution that has been used in a processing operation, a buffer that has been used in a processing operation, or a combination thereof), and may comprise additional reservoirs, if desired. When it is desired to withdraw a fluid from a cell culture device, a microprocessor controls a vacuum pump which, when activated, provides a vacuum that pumps the fluid (e.g., cell culture medium) from a cell culture device, through a pipette, through a fluid pathway, and into the reservoir in fluid communication with the pipette. As illustrated in FIG. 2, preferably a reservoir 70, into which is pumped one or more fluids, may further comprise a fluid level sensor 74 as known in the art to generate a signal (whether a feedback signal to the microprocessor and/or an audio signal for alerting a user) when the fluid reaches a predetermined level in the reservoir. A fluid level sensor may include, but is not limited to, a capacitive fluid level proximity sensor placed at a predetermined level in the reservoir. It will be apparent to one skilled in the art that a reservoir of the plurality of reservoirs may be located either within biochamber 14 of automated cell management system 10 (e.g., affixed to a wall of the chamber), or outside of biochamber 14 of automated cell management system 10 (e.g., affixed to, as part of, an exterior surface of the automated cell management system; or free-standing or separate from the structure of the automated cell management system).

Automated cell management system 10 may further comprise a discharge station 80 for discharging cell culture devices from biochamber 14, and more preferably, for enabling removal of cell culture devices from the automated cell management system. In one embodiment, discharge of cell culture devices is performed manually. Thus, in this embodiment the discharge station comprises opening an access 18 (a securable, sealable panel or door) to access biochamber 14. Cell culture devices may then be manually removed from the storage array or any other location accessible in biochamber 14. After manually removing the one or more cell culture devices to be discharged from the automated cell management system, access 18 may then be closed to form a closed environment for biochamber 14. The user then may manually enter into a microprocessor the specific position from which a specific cell culture device was removed to complete the tracking of each cell culture device that was removed from the automated cell management system. Alternatively, and in a more preferred embodiment, discharging of a cell culture device is performed automatically, in which cell culture devices are discharged from the automated cell management system. For example, as illustrated in FIG. 2, discharge station may comprise a sealable access which, when open, allows a cell culture device to be fed through the access slot and discharged to the exterior of the automated cell management system. Alternatively, the discharge station may comprises a sealable access that, when open, allows a cell culture device to be discharged from the biochamber and into a compartment (which may further comprise a receptacle for collecting discharged cell culture devices) separate from the biochamber. In a preferred embodiment, handling device 40, gripping a cell culture device, feeds the cell culture device through an open slot of discharge station 80 in discharging a cell culture device from the biochamber. Cell culture devices discharged from the biochamber may be considered "discharged cell culture devices". In one embodiment, the discharge station may further comprises a receptacle in which is collected the discharged cell culture devices. In that regard, a user may then, as periodically as desired, access the receptacle to properly dispose of the discharged cell culture devices. It will be apparent to one skilled in the art that a cell culture device may be discharged, via use of the handling device, from any location within the biochamber of the automated cell management system including, but not limited to, the storage array, a processing station, a centrifuge, and an evaluation station. A microprocessor may be used for controlling the discharging process, or operation of the discharge station. For example, a microprocessor may be used for controlling the opening and closing of slot, or access, or a combination thereof, through which a cell culture device is discharged. Additionally, in a preferred embodiment wherein handling device further comprises an identification code reader, the identification code of the cell culture device being discharged may be read and then recorded for tracking purposes, and further, such information may be sent to, processed and stored by, a microprocessor.

Automated cell management system 10 may further comprises a microprocessor 90. In referring to FIG. 8, microprocessor controls and coordinates the operation of the automated cell management system, and provides for data storage related to programming, functions, and collection of data (e.g., resulting from evaluation). Programmable commands from the user are inputted into the microprocessor 90 via a keyboard 92 and/or any additional control buttons (including a touch-sensitive screen display). Information regarding the operation, or programming, or function, or a combination thereof, of the automated cell management system (e.g., relative to one or more of environment controlling mechanism 16, sealed accesses 18, storage array 20, handling device 40, loading station 50, processing station 60, mechanism 120 for tracking cell culture devices within the automated cell management system (e.g., identification code reader and/or position sensors), reservoirs 70, evaluation station 85, centrifuge 100) are displayed on a display panel 94, and may be stored in memory 96. As apparent to one skilled in the art, suitable components of microprocessors (including circuitry, data storage drive, display, and keyboard) are conventional in the art. Microprocessor 90 may be built into the automated cell management system (see, e.g., FIG. 1), or may comprise a host computer (e.g., typical workstation, or personal computer, or other suitable computer platform) in operative communication with the automated cell management system.

Automated cell management system 10 may further comprise one or more evaluation stations for measuring one or more cell culture parameters. In one embodiment, an evaluation station 85 may comprise an imaging device for effecting measurements in colorimetry (e.g., using a photometer), light scatter, light transmission, for observing cultured cells (e.g., number, morphology, or a combination thereof) or other optically detectable and measurable parameters as standard in the art. A cell culture device may be moved to, and positioned with respect to, an evaluation station by the handling device so that the contents of the cell culture device may be evaluated by an imaging device. The imaging device may be selected from conventional components known in the art. For example, the imaging device may comprise one or more standard microscope objectives and a light source for phase contrast, or an optical fiber system. The imaging device may further comprise a camera (e.g., CCD camera), an image analyzer, a computer for processing and viewing the image generated, or a combination thereof. To determine cell number, optical density may be measured using an optical densitometer using methods known in the art (e.g., at 590 nm); or alternatively, the evaluation station may comprise a cell counter standard in the art. Measuring the pH of a fluid contained within a culture chamber of a cell culture device may be performed by measuring light absorption of the cell culture (particularly, the cell culture medium containing phenol red) with a photometer (e.g., measuring the absorptions at 440 nm and 560 nm, calculating the ratio of absorptions, and relating that ratio value to a pH value as known by those skilled in the art). Preferably, the cell culture medium and tissue culture medium contain an pH indicator compound that interacts with light (preferably in a spectral range of from about 400 nm to about 700 nm), that has absorption characteristics which changes when exposed to a change in hydronium ion concentration, and therefore can be related to the pH of the medium.

In another embodiment, the imaging device may comprise an image cytometer particularly suited for evaluating anchorage-dependent cells. For example, using a standard cytometer, and with the optical properties of the membrane of cell culture device 22, it is known in the art that images acquired of cultured cells may be used to determine the size and shape of cells, nuclei and key organelles; the number of cells; the distribution and concentration of cellular substances; the organizational relationships of cultured cells (e.g., growth pattern, motility, apoptosis, and the like); and a combination thereof. As known to those skilled in the art, an image cytometer may comprise intensity thresholding, image segmentation, a stable light source, pattern filtering, and a computer for image analysis processing. The image cytometer may further comprise image content analysis function for autofocusing. The operation of the imaging device system may be controlled by microprocessor 90. The microprocessor may further process data input to it from the imaging device. In a preferred embodiment, an evaluation station, of the one or more evaluation stations of the automated cell management system according to the present invention, may be selected from the group consisting of an imaging device, a sensor for measuring a parameter of a cell culture component, and a combination thereof.

The one or more evaluation stations may comprise one or more sensors for measuring a parameter of a cell culture component in the automated cell management system according to the present invention. For example, sensors that may be useful for measuring a parameter of a cell culture component comprising cell culture medium are known in the art for measuring parameters of fluids, wherein the parameters may include, but are not limited to, pH, oxygen content, carbon dioxide content, one or more carbohydrates (e.g., glucose), protein, ions (e.g., $Ca^{++}$), osmolarity, and the like. Each of the one or more sensors may be placed in a fluid pathway in the biochamber through which the cell culture medium or other suitable fluid originating from a culture chamber is flowed so as to come into operative contact with the sensor to effect a measurement, and more preferably in a fluid pathway at a station selected from the group consisting of a processing station, an evaluation station, or a combination thereof. For example, a pH sensor may be used to measure the pH of the cell culture medium. Thus, one or more pH sensors may be in the fluid pathway at a processing station, an evaluation station, or a combination thereof. The one or more evaluation stations may preferably be operatively connected to a microprocessor for processing and storing data generated by evaluating a cell culture in the automated cell management system, in generating a measurement value that can correspond to a parameter of a cell culture component (comprising a parameter of cultured cells, a parameter of the cell culture medium, or a combination thereof).

Automated cell management system 10 may further comprise sterilization means 100 which may include, but is not limited to, a source of irradiation, a source comprising a gas suitable for sterilization, a washing and rinsing mechanism, and a combination thereof. For example, in one embodiment, a source of irradiation comprises one or more lamps capable of emitting ultraviolet (uv) light. The one or more lamps are positioned in the biochamber of the automated cell management system so that the components (e.g., storage array, processing station, handling device, and the like) and desired surfaces (e.g., walls, floor, and the like) within the biochamber that are desired to be sterilized may be exposed to the emitted uv light. As known in the art, uv light rays (e.g., in the wavelength range of from about 200 nm to about 350 nm) can provide a sterilizing effect against microbial contamination. The uv light may be used by itself, or in combination with a gas for sterilization which is flowed into the biochamber (e.g., a gaseous metal oxide such as titanium dioxide, or ethylene oxide gas) from a source, to provide sterilization of desired surfaces and components within the biochamber of the automated cell management system using methods conventional in the art. As known in the art, a source of irradiation may comprise one or more sources for providing a sterilizing beam of gamma irradiation (e.g., in the range of from about 3K rads to about 50K rads) using methods conventional in the art. Thus, the component in the biochamber desired to be sterilized are exposed to an amount of irradiation for a time sufficient to effect sterilization. Alternative to use of a source of irradiation, the sterilization means may comprise a source (e.g., tank or container) comprising a gas suitable for the intended purpose of sterilization as known in the art. As described herein, the gas may then be flowed into the biochamber in exposing desired surfaces and components within the biochamber for a time sufficient to effect sterilization using methods conventional in the art.

A washing and rinsing mechanism may comprise introduction of one or more sterilizing fluids into the biochamber, or components parts therein (e.g., fluid pathways, storage array, and the like), of the automated cell management system. As apparent to those skilled in the art, a sterilizing fluid may include, but is not limited to, high temperature water vapor, a disinfectant solution (e.g., surfactant solution, chemical solution, cleaning solution), and the like. Thus, the components in the biochamber desired to be sterilized are exposed to an amount of the one or more sterilizing fluids for a time sufficient to effect sterilization. As an example and as related to the pipette system, the pipette tips may be washed and rinsed by repeated cycles of aspirating a wash solution (one or more of a sterile physiological solution, or a sterilizing fluid) and dispensing the wash solution (e.g., wherein the wash solution is dispensed to a waste reservoir). Use of a washing and rinsing mechanism may further comprise allowing the washed and rinsed components within the biochamber to dry before use of the automated cell management system after the sterilization cycle.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. An apparatus comprising an automated system for management of cell cultures, the apparatus comprising:
    a housing having a biochamber for providing controlled environmental conditions in which cells may be cultured and manipulated;
    a storage array for accommodating a plurality of cell culture devices, wherein a cell culture device comprises a housing to which is secured at least one gas permeable, liquid impermeable membrane, and wherein a cell culture device further comprises one or more chambers for culturing cells;
    a loading station for introducing cell culture devices into the biochamber;
    a handling device for handling and moving one or more cell culture devices within the biochamber;
    a means for harvesting a cell culture component from a cell culture device, wherein the cell culture component is selected from the group consisting of cultured cells, cell culture medium, and a combination thereof; and
    one or more processing stations for performing a process selected from the group consisting of aspirating a substance from a cell culture device, introducing a substance into the cell culture device, and a combination thereof.

2. The apparatus according to claim 1, further comprising a component selected from the group consisting of
    a mechanism for tracking cell culture devices in relation to the apparatus,
    a centrifuge,
    a plurality of reservoirs which are in fluid communication with one or more stations of the apparatus,
    a discharge station for permitting removal of cell culture devices from the apparatus,
    a microprocessor for controlling functions and programmable operations of the apparatus,
    one or more evaluation stations for measuring one or more cell culture parameters,
    one or more means for sterilization of components and surfaces within the biochamber, and
    a combination thereof.

3. The apparatus according to claim 1, wherein the housing of the apparatus further comprises one or more sealable accesses which is openable to access the biochamber, and closable to form a closed environment within the biochamber.

4. The apparatus according to claim 3, wherein a sealable access of the one or more sealable accesses comprises a transparent panel.

5. The apparatus according to claim 4, wherein the transparent panel permits a user to view the biochamber from outside the apparatus.

6. The apparatus according to claim 1, wherein the environment conditions are controlled by an environment controlling mechanism that controls a parameter selected from the group consisting of temperature, atmospheric gas content, humidity, pressure, airflow, and a combination thereof.

7. The apparatus according to claim 1, wherein the storage array can accommodate a number of cell culture devices, wherein:
    the number comprises at least 50 cell culture devices; and
    the number comprises no more than 1000 cell culture devices.

8. The apparatus according to claim 1, wherein the storage array comprises a plurality of positions, and wherein each position is adapted to receive and hold a cell culture device.

9. The apparatus according to claim 8, wherein each position, of the plurality of positions of the storage array, further comprises a coordinate representative of that position for distinguishing between each position of the plurality of positions.

10. The apparatus according to claim 1, wherein the storage array comprises a capability selected from the group consisting of non-rotatable around its axis, rotatable around its axis, and a combination thereof.

11. The apparatus according to claim 10, wherein the storage array is rotatable, and the storage array comprises a mode selected from the group consisting of in a non-rotating position, and rotating partial revolutions about its axis.

12. The apparatus according to claim 11, wherein the storage array comprises a mode in which the storage array is rotated in partial revolutions about its axis in a process of repositioning the storage array.

13. The apparatus according to claim 11, wherein the storage array comprises a mode in which the storage array is rotated in partial revolutions about its axis in a process of agitation.

14. The apparatus according to claim 11, wherein operation of the storage array is controlled by a microprocessor.

15. The apparatus according to claim 1, wherein the handling device comprises a mechanical gripper.

16. The apparatus according to claim 15, wherein the handling device comprises a mechanical gripper and a mechanical arm joined by a translational joint.

17. The apparatus according to claim 1, wherein operation of the handling device is controlled by a microprocessor.

18. The apparatus according to claim 1, wherein the loading device comprises a motorized infeed conveyor, and an access for receiving cell culture devices during a loading process.

19. The apparatus according to claim 18, wherein the loading device further comprises a loading cassette.

20. The apparatus according to claim 1, wherein operation of the loading device is controlled by a microprocessor.

21. The apparatus according to claim 1, wherein a means for harvesting a cell culture component comprises a centrifuge adapted for centrifuging one or more cell culture devices.

22. The apparatus according to claim 1, wherein a processing station comprises the means for harvesting a cell culture component.

23. The apparatus according to claim 1, wherein a means for harvesting a cell culture component comprises a processing station for dilating a membrane of the cell culture device to which cultured cells are adhered in loosening the cells from the dilated membrane.

24. The apparatus according to claim 23, wherein a means for harvesting a cell culture component further comprises a centrifuge for centrifuging the cell culture device.

25. The apparatus according to claim 1, wherein the substance introduced into or aspirated from a cell culture device at the one or more processing stations comprises a substance selected from the group consisting of a fluid, cells, one or more biological substances, air, and a combination thereof.

26. The apparatus according to claim 1, wherein a processing station, of the one or more processing stations, comprises a pipette system; and wherein a pipette system comprises a plurality of pipettes.

27. The apparatus according to claim 26, wherein the pipette system is in fluid communication with a plurality of reservoirs.

28. The apparatus according to claim 26, wherein each pipette, of the plurality of pipettes, comprises a pipette tip.

29. The apparatus according to claim 1, wherein the process comprises a processing operation selected from the group consisting of initiating a cell culture in a cell culture device, adding tissue culture medium to cells contained in a cell culture device, adding one or more biological substances to cells in a cell culture device, harvesting of a cell culture component from a cell culture device, sampling of a cell culture component from a cell culture device, terminating a cell culture prior to discharge of a cell culture device from the automated system, extracting protein from a cell culture component contained in a cell culture device, extracting nucleic acid from a cell culture component contained in a cell culture device, and a combination thereof.

30. The apparatus according to claim 1, wherein operation of the one or more processing stations is controlled by a microprocessor.

31. The apparatus according to claim 2, wherein the apparatus further comprises a mechanism for tracking cell culture devices in relation to the apparatus; and wherein the mechanism comprises a mechanism selected from the group consisting of an identification code reader, generating coordinates wherein each coordinate is representative of a specific location relative to the apparatus, and a combination thereof.

32. The apparatus according to claim 2, wherein the apparatus further comprises a mechanism for tracking cell culture devices comprising an identification code reader, wherein the identification code reader comprises a barcode reader, and wherein each cell culture device to be tracked has an identification code comprising a barcode.

33. The apparatus according to claim 31, wherein the mechanism for tracking cell culture devices is operatively connected to a microprocessor.

34. The apparatus according to claim 2, wherein the apparatus further comprises a plurality of reservoirs.

35. The apparatus according to claim 34, wherein each reservoir of the plurality of reservoirs has a fluid pathway that comprises fluid communication between the reservoir and a station of the apparatus.

36. The apparatus according to claim 35, wherein fluid flow, in a fluid pathway comprising fluid communication between a reservoir and a station, is controlled by a microprocessor.

37. The apparatus according to claim 34, wherein one or more reservoirs of the plurality of reservoirs has a fluid level sensor.

38. The apparatus according to claim 2, wherein the apparatus further comprises a discharge station.

39. The apparatus according to claim 38, wherein a microprocessor is used for controlling operation of the discharge station.

40. The apparatus according to claim 2, wherein the apparatus further comprises a microprocessor.

41. The apparatus according to claim 40, wherein the microprocessor controls and coordinates the operation of the apparatus.

42. The apparatus according to claim 41, wherein the microprocessor further provides for data storage for information for a process selected from the group consisting of operation of the apparatus, programming of the apparatus, functioning of the apparatus, and a combination thereof.

43. The apparatus according to claim 2, wherein the apparatus further comprises a centrifuge.

44. The apparatus according to claim 43, wherein the centrifuge comprises an upper cover plate and a support plate which, in operative combination, hold and secure a cell culture device.

45. The apparatus according to claim 43, wherein a microprocessor is used for controlling operation of the centrifuge.

46. The apparatus according to claim 2, wherein the apparatus further comprises one or more evaluation stations.

47. The apparatus according to claim 46, wherein an evaluation station, of the one or more evaluation stations, is selected from the group consisting of an imaging device, a sensor for measuring a parameter of a cell culture component, and a combination thereof.

48. The apparatus according to claim 2, wherein the apparatus further comprises one or more means for sterilization of components and surfaces within the biochamber.

49. The apparatus according to claim 48, wherein the one or more means for sterilization is selected from the group consisting of a source of irradiation, a source comprising a gas for sterilization, a washing and rinsing mechanism, and a combination thereof.

50. An apparatus comprising an automated system for management of cell cultures, the apparatus comprising:
  a housing having a biochamber for providing controlled environmental conditions in which cells may be cultured and manipulated, wherein the housing further comprises one or more sealable accesses which is openable to access the biochamber, and closable to form a closed environment within the biochamber;
  a storage array for accommodating a plurality of cell culture devices, wherein a cell culture device comprises a housing to which is secured at least one gas permeable, liquid impermeable membrane and further comprises one or more chambers for culturing cells, and wherein the storage array comprises a plurality of positions with each position being adapted to receive and hold a cell culture device;

a loading station for introducing cell culture devices into the biochamber;

a handling device for handling and moving one or more cell culture devices within the biochamber;

a means for harvesting a cell culture component from a cell culture device, wherein the cell culture component is selected from the group consisting of cultured cells, cell culture medium, and a combination thereof;

one or more processing stations for performing a process selected from the group consisting of aspirating a substance from a cell culture device, introducing a substance into the cell culture device, and a combination thereof;

a plurality of reservoirs; and a microprocessor for controlling functions and programmable operations of the apparatus.

51. The apparatus according to claim 50, further comprising a component selected from the group consisting of:

a mechanism for tracking cell culture devices in relation to the apparatus, a centrifuge, a discharge station for permitting removal of cell culture devices from the apparatus, one or more evaluation stations for measuring one or more cell culture parameters, one or more means for sterilization of components and surfaces within the biochamber, and a combination thereof.

52. The apparatus according to claim 50, wherein each position, of the plurality of positions of the storage array, further comprises a coordinate representative of that position for distinguishing between each position of the plurality of positions.

53. The apparatus according to claim 50, wherein the storage array comprises a capability selected from the group consisting of non-rotatable around its axis, rotatable around its axis, and a combination thereof.

54. The apparatus according to claim 50, wherein the handling device comprises a mechanical gripper.

55. The apparatus according to claim 54, wherein the handling device comprises a mechanical gripper and a mechanical arm joined by a translational joint.

56. The apparatus according to claim 50, wherein a processing station comprises the means for harvesting a cell culture component.

57. The apparatus according to claim 50, wherein the substance introduced into or aspirated from a cell culture device at the one or more processing stations comprises a substance selected from the group consisting of a fluid, cells, one or more biological substances, air, and a combination thereof.

58. The apparatus according to claim 50, wherein a processing station, of the one or more processing stations, comprises a pipette system, wherein a pipette system comprises a plurality of pipettes, and wherein the pipette system is in fluid communication with a plurality of reservoirs.

59. The apparatus according to claim 50, wherein the process comprises a processing operation selected from the group consisting of initiating a c ell culture in a cell culture device, adding tissue culture medium to cells contained in a cell culture device, adding one or more biological substances to cells in a cell culture device, harvesting of a cell culture component from a cell culture device, sampling of a cell culture component from a cell culture device, terminating a cell culture prior to discharge of a cell culture device from the automated system, extracting protein from a cell culture component contained in a cell culture device, extracting nucleic acid from a cell culture component contained in a cell culture device, and a combination thereof.

60. The apparatus according to claim 50, wherein each reservoir of the plurality of reservoirs has a fluid pathway that comprises fluid communication between the reservoir and a station of the apparatus.

61. The apparatus according to claim 51, wherein the apparatus further comprises a mechanism for tracking cell culture devices in relation to the apparatus; and wherein the mechanism comprises a mechanism selected from the group consisting of an identification code reader, generating coordinates wherein each coordinate is representative of a specific location relative to the apparatus, and a combination thereof.

62. The apparatus according to claim 51, wherein the apparatus further comprises a mechanism for tracking cell culture devices comprising an identification code reader, wherein the identification code reader comprises a barcode reader, and wherein each cell culture device to be tracked has an identification code comprising a barcode.

63. The apparatus according to claim 51, wherein the apparatus further comprises a discharge station.

64. The apparatus according to claim 51, wherein the apparatus further comprises one or more evaluation stations.

65. The apparatus according to claim 64, wherein an evaluation station, of the one or more evaluation stations, is selected from the group consisting of an imaging device, a sensor for measuring a parameter of a cell culture component, and a combination thereof.

66. The apparatus according to claim 51, wherein the apparatus further comprises a centrifuge.

67. The apparatus according to claim 66, wherein the centrifuge comprises an upper cover plate and a support plate which, in operative combination, hold and secure a cell culture device.

68. The apparatus according to claim 51, wherein the apparatus further comprises one or more means for sterilization of components and surfaces within the biochamber.

* * * * *